(12) United States Patent
Trupke

(10) Patent No.: US 9,157,863 B2
(45) Date of Patent: Oct. 13, 2015

(54) SEPARATION OF DOPING DENSITY AND MINORITY CARRIER LIFETIME IN PHOTOLUMINESCENCE MEASUREMENTS ON SEMICONDUCTOR MATERIALS

(71) Applicant: BT Imaging Pty Ltd, Redfern, New South Wales (AU)

(72) Inventor: Thorsten Trupke, Coogee (AU)

(73) Assignee: BT IMAGING PTY LTD., New South Wales (AU)

( * ) Notice: Subject to any disclaimer, the term of this patent is extended or adjusted under 35 U.S.C. 154(b) by 0 days.

(21) Appl. No.: 14/256,480

(22) Filed: Apr. 18, 2014

(65) Prior Publication Data

US 2014/0224965 A1 Aug. 14, 2014

Related U.S. Application Data

(63) Continuation of application No. 13/384,970, filed as application No. PCT/AU2010/000908 on Jul. 19, 2010, now Pat. No. 8,742,372.

(30) Foreign Application Priority Data

Jul. 20, 2009 (AU) ................................ 2009903369

(51) Int. Cl.
  *G01N 21/64* (2006.01)
  *H01L 21/66* (2006.01)

(52) U.S. Cl.
  CPC ............ *G01N 21/6489* (2013.01); *H01L 22/12* (2013.01)

(58) Field of Classification Search
  CPC .......... G01N 21/6408; G01N 21/6456; G01N 21/6489; G01N 21/9505
  USPC ....................................................... 250/459.1
  See application file for complete search history.

(56) References Cited

U.S. PATENT DOCUMENTS 4,202,491 A * 5/1980 Suzuki ........................ 235/491

5,006,717 A * 4/1991 Tsutsu et al. ............... 250/484.2

(Continued)

FOREIGN PATENT DOCUMENTS

| CN | 201273880 Y | 7/2009 |
|---|---|---|
| GB | 2 306 640 A | 5/1997 |

(Continued)

OTHER PUBLICATIONS

Taiwanese Office Action received in corresponding Taiwanese Application No. 99123819 dated Jul. 15, 2014.
Trupke et al., "Photoluminescence Characterization of Silicon Wafers and Silicon Solar Cells", 18th Workshop on Crystalline Silicon Solar Cells & Modules, 2008.

(Continued)

*Primary Examiner* — Kiho Kim
(74) *Attorney, Agent, or Firm* — Mattingly & Malur, PC

(57) ABSTRACT

Methods are presented for separating the effects of background doping density and effective minority carrier lifetime on photoluminescence (PL) generated from semiconductor materials. In one embodiment the background doping density is measured by another technique, enabling PL measurements to be analyzed in terms of effective minority carrier lifetime. In another embodiment the effective lifetime is measured by another technique, enabling PL measurements to be analyzed in terms of background doping density. In another embodiment, the effect of background doping density is removed by calculating intensity ratios of two PL measurements obtained in different spectral regions, or generated by different excitation wavelengths. The methods are particularly useful for bulk samples such as bricks or ingots of silicon, where information can be obtained over a much wider range of bulk lifetime values than is possible with thin, surface-limited samples such as silicon wafers. The methods may find application in solar cell manufacturing.

21 Claims, 13 Drawing Sheets

(56) References Cited

U.S. PATENT DOCUMENTS

| | | | | |
|---|---|---|---|---|
| 5,381,016 A | * | 1/1995 | Moriya | 250/458.1 |
| 7,113,276 B1 | | 9/2006 | Higgs et al. | |
| 2002/0050595 A1 | | 5/2002 | Ono et al. | |
| 2007/0007466 A1 | | 1/2007 | Laurent et al. | |
| 2010/0209632 A1 | * | 8/2010 | Weisman et al. | 428/29 |

FOREIGN PATENT DOCUMENTS

| | | |
|---|---|---|
| JP | 2002-026095 A | 1/2002 |
| TW | 200637021 A | 10/2006 |
| WO | 2007-041758 A1 | 4/2007 |
| WO | 2008-014537 A1 | 2/2008 |
| WO | 2009/026661 A1 | 3/2009 |
| WO | 2009-121133 A1 | 10/2009 |
| WO | 2010-130013 A1 | 11/2010 |

OTHER PUBLICATIONS

Trupke, "Influence of Photon Reabsorption on Quasi-Steady-State Photoluminescence Measurements on Crystalline Silicon", Journal of Applied Physics 100, 2006, pp. 063531-1-063531-8.

Bowden et al., "Determining lifetime in silicon blocks and wafers with accurate expressions for carrier density", Journal of Applied Physics, 102, 2007, pp. 124501-1-124501-7.

Shumacher et al., "Photoluminescence Characterization of Ultraiiigii Purity Silicon", Journal of Electric Materials, vol. 18, No. 6, 1989, pp. 681-683.

Lakhov et al., "Scanning Photoluminescence of GaAlAs/GaAs/GaAlAs Binary Heterostructure", Measurement Techniques, vol. 43, No. 5, 2000, pp. 422-424.

International Search Report for PCT/AU2010/000908 dated Oct. 14, 2010.

* cited by examiner

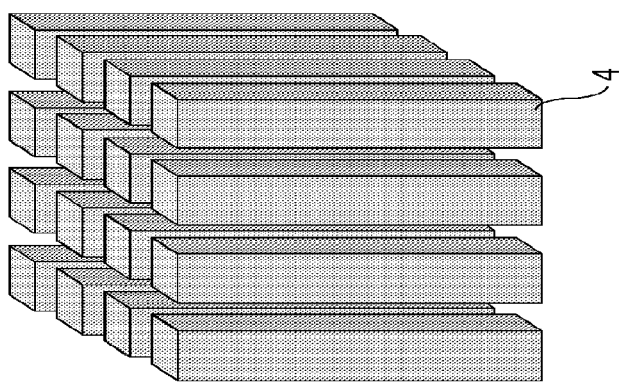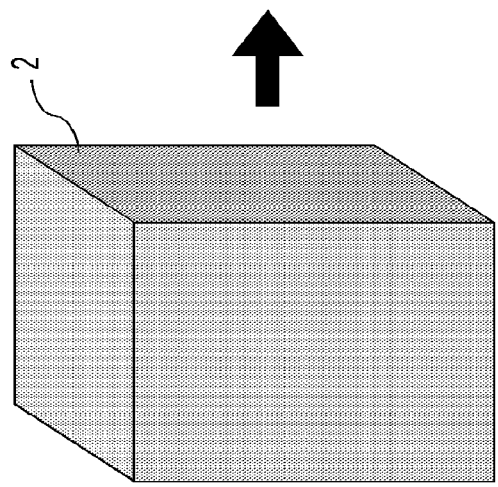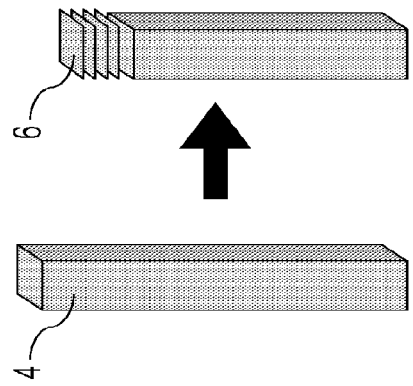
Fig 1

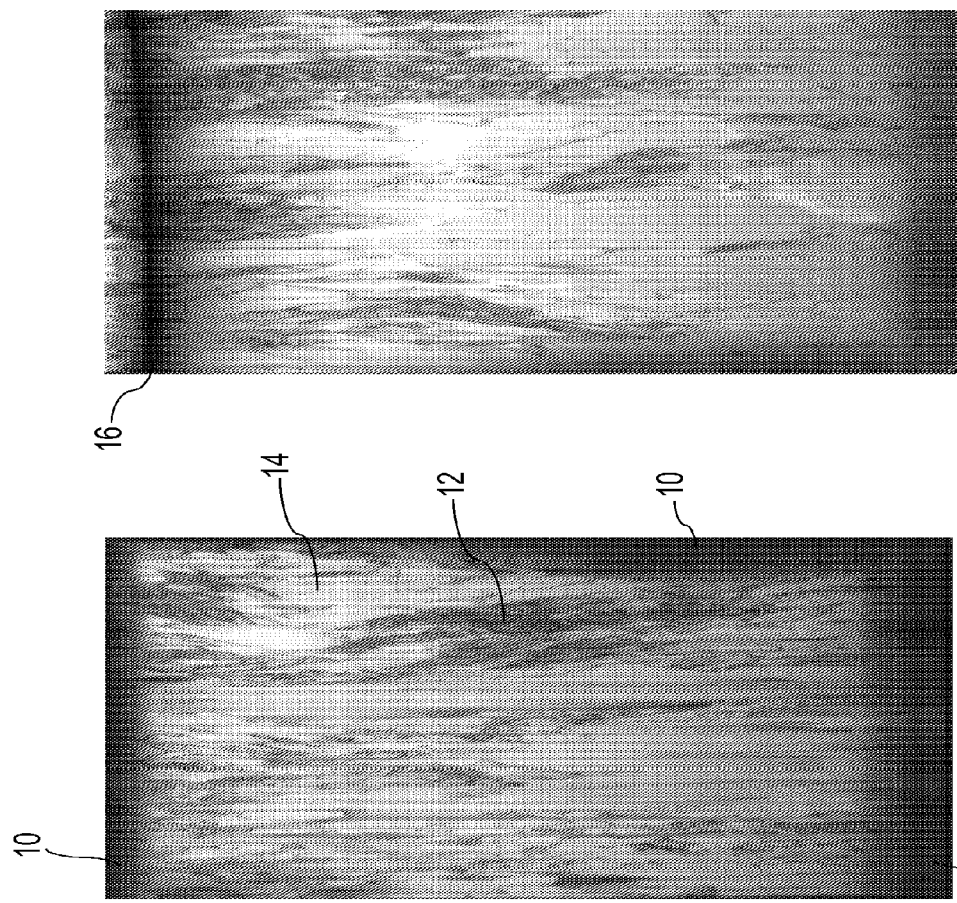

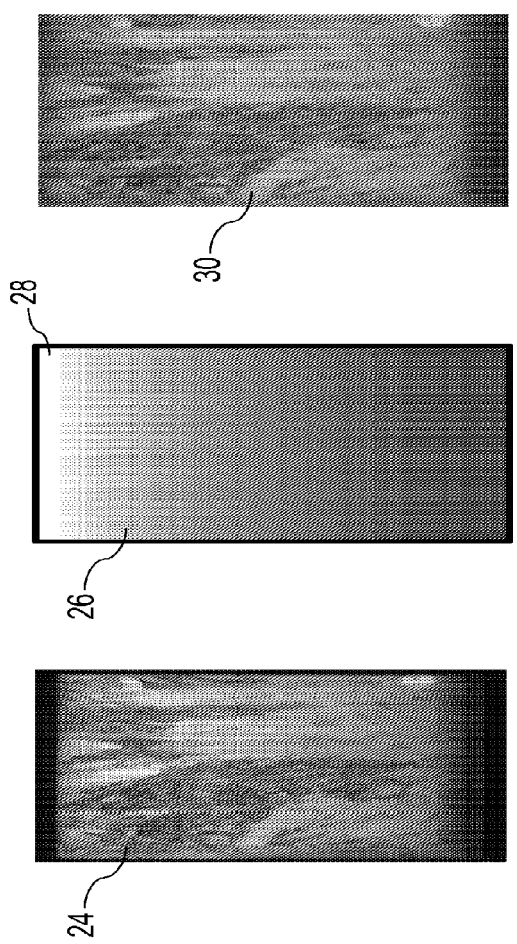
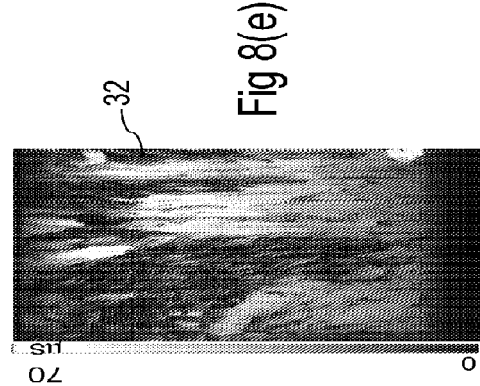
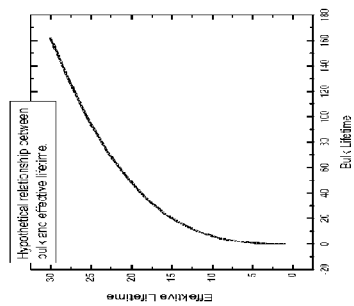

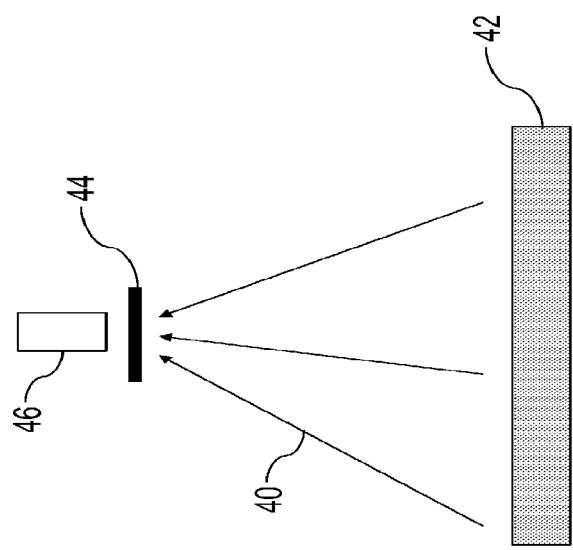

SEPARATION OF DOPING DENSITY AND MINORITY CARRIER LIFETIME IN PHOTOLUMINESCENCE MEASUREMENTS ON SEMICONDUCTOR MATERIALS

This application is a continuation of U.S. patent application Ser. No. 13/384,970, filed Mar. 30, 2012, which is a 371 of International Application No. PCT/AU2010/000908, filed Jul. 19, 2010, which claims priority to Australian Patent Application No. 2009903369, filed Jul. 20, 2009. The entire disclosures of these applications are incorporated herein by reference.

FIELD OF THE INVENTION

The present invention relates to the characterisation of semiconductor materials using photoluminescence measurements, and in particular to techniques for separating the effects of doping density and minority carrier lifetime on the photoluminescence signal. The invention has been developed primarily for the characterisation of bulk (i.e. non-wafer) silicon samples, however it will be appreciated that the invention is not limited to this particular field of use.

BACKGROUND OF THE INVENTION

Commercial wafer based solar cells are made from typically 10×10 cm² up to 22×22 cm² silicon wafers. As illustrated in FIG. 1, a cast multicrystalline silicon block 2 (also known as an ingot), typically 1×1×0.7 m³ in size, is sawn into square (10×10 cm² up to 22×22 cm²) shaped columns 4 (commonly known as bricks), which are then sawn into individual wafers 6, each typically 120-250 µm thick. An ingot is usually sawn into 4×4 or 5×5 bricks. Solar cells can be made from multicrystalline silicon or monocrystalline silicon, with different techniques used for growing multicrystalline and monocrystalline silicon ingots.

For wafer manufacturers it is of interest to characterise the electronic and structural properties of ingots or bricks prior to wafer slicing. It is commonly known that cast multicrystalline (mc) silicon ingots have increased impurity concentration within the silicon in the outside regions of the ingot, i.e. at the bottom, top and sides. At the bottom and the sides this is the result of diffusion of impurities from the crucible walls into the ingot, while at the top it is caused by segregation of impurities towards the upward-moving top liquid phase during crystallisation of the ingot. A result of the increased impurity concentration is reduced electronic material quality, described by a lower effective minority carrier lifetime. FIG. 2 shows in side view a typical effective minority carrier lifetime distribution in a cast mc silicon ingot, showing an area of mostly high effective lifetime material 8 in the centre and regions of low lifetime 10 at the top, bottom and sides.

Experimental techniques that are currently in use for characterisation of bricks include infrared (IR) transmission and minority carrier lifetime scanning. In the former technique, the transmission of sub-band gap light through the brick is measured from different directions with an IR camera that is sensitive to the sub band-gap spectral range (wavelengths>1100 nm for silicon), providing three-dimensional information about the density and position of inclusions such as silicon carbide (SiC) and silicon nitride ($Si_3N_4$).

Several experimental techniques exist for measuring the effective minority carrier lifetime, including both transient and quasi steady state photoconductance (QSSPC) and microwave photoconductance decay (µ-PCD). These techniques measure the effective minority carrier lifetime, which is an effective sample characteristic parameter affected by both the bulk material quality (i.e. the bulk minority carrier lifetime) and surface recombination. Especially on samples with unpassivated surfaces, such as as-cut wafers, the effective lifetime is usually strongly affected or dominated by surface recombination. Two-dimensional information about lateral variations of the effective lifetime, e.g. on one surface of a brick, can be obtained by using the above methods in a scanning mode, generating a map via point by point scanning in a manual or automated fashion. In some cases, such as QSSPC, the measured effective lifetime data can be converted into bulk lifetime data over a limited range by using predetermined relationships between bulk lifetime and effective lifetime.

Although the effective minority carrier lifetime is the more easily measured quantity, the bulk minority carrier lifetime is the more important quantity for photovoltaic applications because: (a) the impact of surface recombination is significantly reduced in subsequent processing via removal of low lifetime surface material and surface passivation; and (b) bulk lifetime, unlike effective lifetime on an unpassivated sample, determines both the voltage and the current of a finished solar cell. Especially for unpassivated samples with high surface recombination, it is therefore important to be able to convert an as-measured effective lifetime to bulk lifetime.

Another important aspect of minority carrier lifetime is its dependence on the injection level. The bulk lifetime is determined by various recombination mechanisms, including defect recombination, radiative recombination and Auger recombination. The recombination rate via these mechanisms is non-linear in the concentration of minority carriers and as a result the bulk minority carrier lifetime itself depends on the density of minority carriers. Ideally therefore, experimental data for the minority carrier lifetime should be reported as a function of injection level, whether lifetime is area-averaged or spatially resolved. However, since representation of data as a function of two independent parameters (position and injection level) is difficult, spatially resolved data such as lifetime images or lifetime maps are often reported only for a single injection level for each point.

Upgraded Metallurgical Grade (UMG) silicon is a prospective material for achieving significant cost reductions in silicon wafer-based photovoltaics. A commonly observed feature of UMG ingots and bricks is an inversion of the background doping density that occurs from the bottom to the top of an ingot, caused by the presence of significant quantities (densities) of both phosphorous and boron in the feedstock. Due to the different segregation coefficients of these dopants, their incorporation into the crystal occurs at different rates. As a result UMG ingots are generally found to be p-type at the bottom and n-type at the top, with a so called 'compensated region' in between that is effectively undoped or only very lightly doped. A method to gain information quickly about the position and shape of the transition region is required, since wafers from that region and the n-type wafers from above that region cannot be used in conventional screen printed solar cell production lines, which normally use p-type wafers.

The ability to measure the effective lifetime of silicon wafers using photoluminescence (PL) imaging has been described in published PCT patent application No WO 2007/041758 A1 entitled 'Method and System for Inspecting Indirect Bandgap Semiconductor Structure' and incorporated herein by reference. The measurable luminescence intensity in PL imaging on semiconductor materials is determined by the rate of spontaneous emission $r_{sp}$, which can generally be assumed to be linear in the product of the electron (n) and hole (p) concentrations, i.e. $r_{sp}=B*n*p$, where B is a proportionality factor referred to in the literature as the radiative recombination coefficient. In PL imaging applications on silicon samples, particularly on unpassivated surfaces, the condition of low level injection is generally fulfilled, which means that the excess minority carrier concentration $\Delta n$ is significantly smaller than the background doping concentration $N_d$, i.e. $\Delta n \ll N_d$. In this case the total minority carrier density is given to very good approximation by $\Delta n$ and the majority carrier density by $N_d$. As a result the emitted luminescence is proportional to the excess minority carrier density and the background doping density so that $r_{sp}=B*\Delta n*N_d$. Under quasi steady state conditions, i.e. where the generation and recombination rates are equal, the effective minority carrier lifetime is inversely proportional to the generation rate G and proportional to the minority carrier density such that $\tau_{eff}=\Delta n/G$, which results in $r_{sp}=B*G*\tau_{eff}*N_d$. The rate of spontaneous emission and thereby the PL intensity under specific illumination intensity (i.e. for given G) is thus proportional to the product of the effective minority carrier lifetime and the doping density.

In previous PL imaging applications the influence of the doping density on PL intensities has been described, but an implicit assumption of laterally constant background doping density over the sample area was made. For example in T. Trupke, R. A. Bardos and J. Nyhus, 'Photoluminescence characterisation of silicon wafers and silicon solar cells', 18*th Workshop on Crystalline Silicon Solar Cells & Modules* 2008, Vail, USA, the influence of the background doping density on the absolute luminescence intensity between different samples and its impact on the calibration of PL images has been discussed. For many commonly used silicon wafers (e.g. conventional cast mc wafers) the assumption that the background doping density is constant laterally across the sample area is well justified, allowing interpretation of PL images in terms of lateral variations of the excess minority carrier density $\Delta n$ in all cases where the surface properties of the sample (texturing and antireflection coating) are sufficiently homogeneous.

However there are several types of sample where the assumption of a laterally constant background doping density is not justified. These include:

(i) Side facets of common mc silicon bricks or ingots. Doping density variations $N_D(x)$ within typical mc silicon bricks and ingots can often be significant. In many cases the variation of the doping density along the growth direction can be described by the Scheil equation which is derived from considering the thermodynamic potential of the dopant in the two phases of the solidifying silicon casting block:

$$N_D(x)=N_D(0)\cdot K_{eff}(1-x)^{K_{eff}-1}$$

In this equation $K_{eff}$ is a coefficient characteristic of the dominant dopant atom and the crystal host and x is the relative height within the brick or ingot (x=0 corresponds to the bottom, x=1 to the top). For example for a typical 25 cm high boron doped (p-type) silicon ingot or brick, the doping density increases by typically 30%-40% relative from the bottom to the top.

(ii) Side facets of UMG silicon bricks or otherwise intentionally or unintentionally doping-compensated ingots or bricks. Strong variations of the effective doping density are observed, with a transition region from effective p-type doping to n-type doping.

(iii) Wafers from UMG bricks. The transition region from p-type to n-type is not strictly parallel to the direction in which wafers are cut from the ingot, because of a typically curved solid-liquid interface near the crystallisation front. Wafers from near the transition region will therefore show strong variations in the doping density within each wafer, some of them even showing a transition from p-type to n-type within a single wafer.

(iv) Vertical samples from Czochralsky (Cz) grown monocrystalline ingots. Vertical variations in the background doping density will show up on PL images taken on silicon ingots or wafers cut vertically from such ingots.

(v) Monocrystalline wafers, particularly n-type Cz wafers, often exhibit circular variations (striations) in the doping density. These can be seen particularly clearly in luminescence images taken on unpassivated wafers, since the effective lifetime is surface limited and thus almost constant across the wafer area. Even small variations in doping density are therefore clearly visible in luminescence images.

(vi) There are various other new and more exotic types of silicon ingot manufacturing processes in development that may become mainstream. Examples include BP Solar's cast 'mono-crystalline' process and Muto's direct chemical formation process. Each new process for making crystalline silicon blocks will have idiosyncrasies in dopant concentrations and lifetime variations.

Where a constant background doping density can no longer be assumed, the intensity variation in a PL image is determined by the product of 1) the doping density and 2) the effective minority carrier lifetime. To get reliable information about spatial variations of one of these two quantities, the PL signal therefore needs to be corrected or normalised for absolute or relative variations of the other quantity, which can be measured directly or inferred.

SUMMARY OF THE INVENTION

It is an object of the present invention to overcome or ameliorate at least one of the disadvantages of the prior art, or to provide a useful alternative. It is an object of the present invention in its preferred form to provide improved methods for characterising semiconductor materials, and in particular bulk silicon samples, using photoluminescence measurements.

In accordance with a first aspect of the present invention there is provided a method of conducting an analysis of a semiconductor material, said method including the steps of: (a) exciting said material to produce photoluminescence; (b) measuring the intensity of the photoluminescence emitted from said material; (c) normalising the measured photoluminescence intensity with regard to variations in the background doping density of said material to obtain a normalised photoluminescence intensity; and (d) analysing said normalised photoluminescence intensity in terms of one or more properties of said material.

Preferably a substantial area of the material is excited, and the measuring step images the photoluminescence emitted from the area. In preferred embodiments the material is a silicon ingot or a silicon brick, and the method is applied to at least one side facet of the ingot or brick. In one preferred form the background doping density is measured experimentally. Alternatively, the background doping density is determined empirically or calculated using a theoretical relationship. Preferably, the normalised photoluminescence intensity is interpreted as a measure of the effective minority carrier lifetime of the material. Alternatively, the normalised photoluminescence intensity is converted to a measure of the bulk minority carrier lifetime of the material using a predetermined theoretical relationship between bulk lifetime and normalised photoluminescence intensity. In preferred embodiments the theoretical relationship is applied to multiple samples of said material with similar surface preparation. In other preferred embodiments the property is the area or volume density of dislocations in the material.

In accordance with a second aspect of the present invention there is provided a method of conducting an analysis of a silicon ingot or brick, said method including the steps of: (a) exciting at least a portion of at least one side facet of said silicon ingot or brick to produce photoluminescence; (b) obtaining at least one image of the photoluminescence emitted from said at least one portion of at least one side facet; and (c) interpreting said at least one image in terms of variations in the area density of dislocations in said silicon ingot or brick.

In one preferred form the photoluminescence images obtained from different side facets of the ingot or brick are analysed to obtain an estimated area density of dislocations within wafers subsequently cut from the ingot or brick. In another preferred form, at least one photoluminescence image is used to highlight regions of the ingot or brick of insufficient quality for wafer production.

In accordance with a third aspect of the present invention, there is provided a method of conducting an analysis of a silicon ingot or brick, said method including the steps of: (a) exciting at least one side facet of said silicon ingot or brick to produce photoluminescence; (b) obtaining at least one image of the photoluminescence emitted from said at least one side facet; and (c) interpreting said at least one image to identify low effective and/or bulk minority carrier lifetime regions within said ingot or brick.

In accordance with a fourth aspect of the present invention, there is provided a method of conducting an analysis of a semiconductor material, said method including the steps of (a) exciting a portion of said material to produce photoluminescence; (b) measuring the distribution of the photoluminescence emitted from said portion; (c) normalising the measured photoluminescence distribution with regard to variations in the effective minority carrier lifetime across said portion; and (d) analysing the normalised photoluminescence distribution in terms of variations in the background doping density of said material across said portion.

Preferably, the material is a silicon ingot or a silicon brick, and the method is applied to at least one side facet of the ingot or brick. The portion is preferably in the form of a line scan or a two-dimensional area. The method is preferably applied to an ingot, brick or wafer of upgraded metallurgical grade silicon. Preferably, the position of a minimum in the distribution of the photoluminescence is fitted to obtain the ratio of donor and acceptor concentrations in the feedstock of the upgraded metallurgical grade silicon. In one preferred form the step of normalising with regard to variations in effective lifetime is omitted, and the photoluminescence distribution is interpreted in terms of background doping variations. Preferably, the position of a minimum in the photoluminescence distribution is used to identify the position of a transition region from p-type to n-type in upgraded metallurgical grade silicon.

In accordance with a fifth aspect of the present invention there is provided a method of conducting an analysis of a silicon ingot or brick, said method including the steps of: (a) obtaining at least two photoluminescence measurements of at least one side facet of said silicon ingot or brick, said at least two photoluminescence measurements being obtained with different detection wavelength bands; (b) calculating intensity ratios between at least two of said photoluminescence measurements; and (c) converting said intensity ratios into bulk lifetime or bulk diffusion length using a predetermined theoretical relationship. Preferably, the different detection wavelength bands are provided by one or more dielectric filters, and the method further comprises the step of normalising the photoluminescence measurements or the intensity ratios for angular variations in the transmission of the one or more dielectric filters.

According to a sixth aspect of the present invention, there is provided a method of conducting an analysis of a silicon ingot or brick, said method including the steps of: (a) obtaining at least two photoluminescence measurements of at least one side facet of said silicon ingot or brick, the photoluminescence in said at least two photoluminescence measurements being generated with different excitation wavelengths; (b) calculating intensity ratios between at least two of said photoluminescence measurements; and (c) converting said intensity ratios into bulk lifetime or bulk diffusion length using a predetermined theoretical relationship.

In any of the above aspects of the present invention, the photoluminescence measurements or images are preferably used as a cutting guide in wafer production or as a guide in wafer production to sort wafers into quality bins. Alternatively, the information obtained from the method is used to improve the manufacturing of silicon bricks or ingots, or to determine the price of wafers derived from the material, or to obtain feedback on feedstock quality in the production of silicon wafers.

According to a seventh aspect of the present invention, there is provided a system for conducting an analysis of a semiconductor material, said system including: a photodetection unit for obtaining at least one image or line scan of photoluminescence generated from a surface of said material; and a processor for normalising the measured photoluminescence intensity with regard to variations in the background doping density across said surface, and for analysing the normalised photoluminescence intensity in terms of one or more properties of said material.

According to an eighth aspect of the present invention, there is provided a system for conducting an analysis of a silicon ingot or brick, said system including: a photodetection unit for obtaining at least one image or line scan of photoluminescence generated from at least one side facet of said silicon ingot or brick; and a processor for interpreting said at least one photoluminescence image or line scan in terms of variations in the area density of dislocations in said silicon ingot or brick.

According to a ninth aspect of the present invention, there is provided a system for conducting an analysis of a silicon ingot or brick, said system including: a photodetection unit for obtaining at least one image or line scan of photoluminescence generated from at least one side facet of said silicon ingot or brick; and a processor for interpreting said at least one photoluminescence image or line scan to identify defect-rich low effective and/or bulk minority carrier lifetime regions within said ingot or brick.

According to a tenth aspect of the present invention, there is provided a system for conducting an analysis of a semiconductor material, said system including: a photodetection unit for obtaining at least one image or line scan of photoluminescence generated from a surface of said material; and a processor for normalising the measured photoluminescence intensity in each part of said image or line scan with regard to variations in the effective minority carrier lifetime across said surface, and for analysing the normalised photoluminescence image or line scan in terms of variations in the background doping density across said surface.

According to an eleventh aspect of the present invention, there is provided a system for conducting an analysis of a silicon ingot or brick, said system including: a photodetection unit for obtaining at least two measurements of photoluminescence generated from at least one side facet of said silicon ingot or brick, said at least two measurements being obtained with different detection wavelength bands; and a processor for calculating intensity ratios between at least two of said measurements, and for converting said intensity ratios into bulk lifetime or bulk diffusion length using a predetermined theoretical relationship. Preferably, the system further includes one or more dielectric filters for providing the different detection wavelength bands, wherein the processor is further configured to normalise the measurements or the intensity ratios for angular variations in the transmission of the one or more dielectric filters.

According to a twelfth aspect of the present invention, there is provided a system for conducting an analysis of a silicon ingot or brick, said system including: first and second excitation units emitting first and second wavelengths for generating photoluminescence from at least one side facet of said silicon ingot or brick; a photodetection unit for obtaining first and second measurements of photoluminescence generated with said first and second excitation wavelengths; and a processor for calculating intensity ratios between said first and second measurements, and for converting said intensity ratios into bulk lifetime or bulk diffusion length using a predetermined theoretical relationship.

Preferably, the system according to any one of the seventh to twelfth aspects of the present invention further includes: an optical source emitting light with wavelength longer than the band-gap of silicon or of said semiconductor material; and a detector for measuring the transmission of said light through said silicon or semiconductor material.

In any one of the seventh to twelfth aspects of the present invention, the photodetection unit preferably includes a silicon camera. Alternatively, the photodetection unit includes an InGaAs camera.

According to a thirteenth aspect of the present invention, there is provided a system when used to implement the method according to any one of the first to sixth aspects of the present invention.

BRIEF DESCRIPTION OF THE DRAWINGS

Benefits and advantages of the present invention will become apparent to those skilled in the art to which this invention relates from the subsequent description of exemplary embodiments and the appended claims, taken in conjunction with the accompanying drawings, in which:

FIG. 1 illustrates the sawing of silicon ingots into bricks and wafers;

FIG. 3 shows a PL image of the side facet of a conventional cast multicrystalline p-type silicon brick;

FIG. 4 shows a PL image of the side facet of a multicrystalline UMG silicon brick;

FIGS. 8(a) to 8(e) illustrate the conversion of a raw PL image of the side facet of a p-type silicon brick (FIG. 8(a)) to a bulk lifetime image (FIG. 8(e));

FIG. 11 illustrates how PL emission from an extended sample encounters an optical filter at a range of incidence angles;

DETAILED DESCRIPTION

Figure 2:
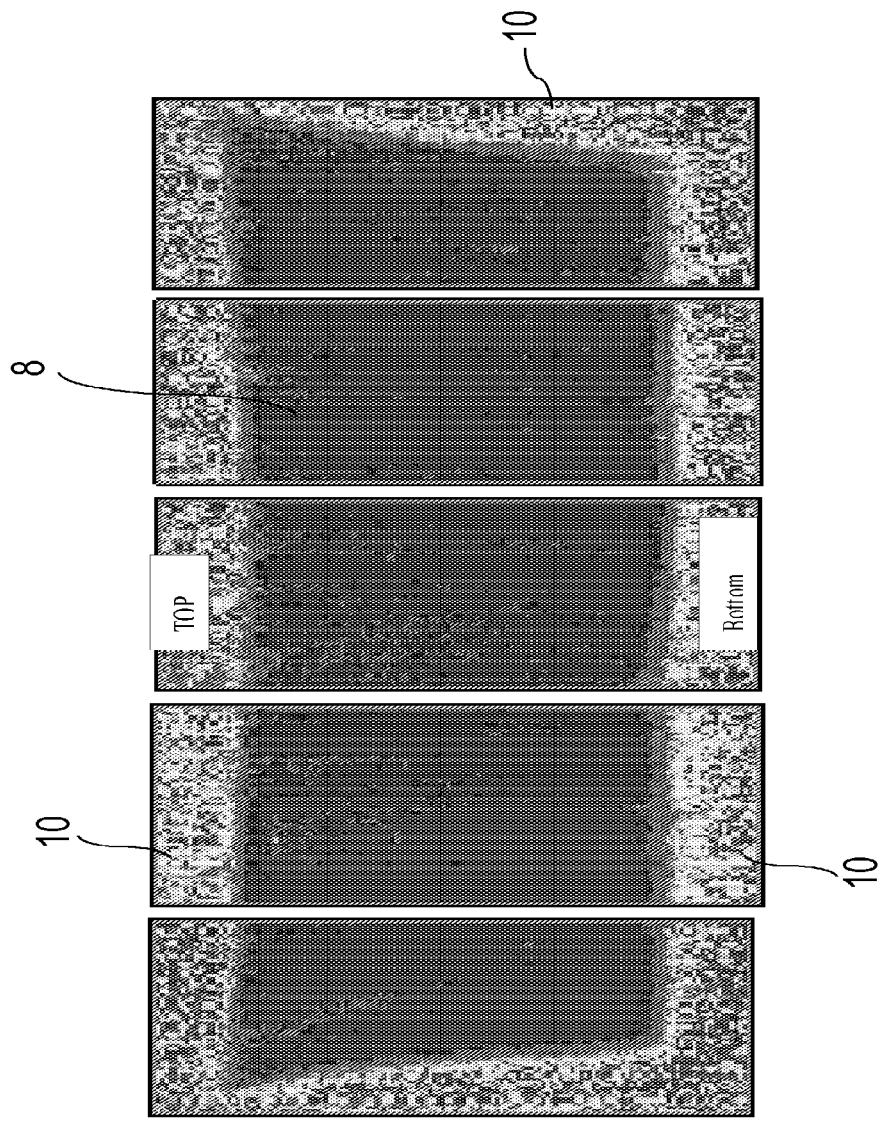
FIG. 2 is a cross sectional side view of a silicon ingot illustrating the typical variation of effective minority carrier lifetime.

Preferred embodiments of the invention will now be described, by way of example only, with reference to the accompanying drawings.

The present invention relates mainly to PL imaging measurements on 'bulk' silicon samples (e.g. bricks and ingots) prior to cutting into wafers. Specific advantages in relation to extracting bulk lifetime information from PL images on bricks in comparison to wafers are disclosed. The present invention details the following principal ideas, which will be described in more detail and in the same sequence below:

1.) Using information about the background doping and its spatial variation to normalise the PL image and thereby obtain more accurate quantitative information on effective or bulk lifetime variations. Specific benefits of PL imaging on bricks/ingots compared to wafer measurements for determination of bulk lifetime images, especially the ability to obtain bulk information over a much wider range of bulk lifetime values and at a well defined injection level, are disclosed.

2.) The relative variation of the PL intensity, even without normalising for variations of the background doping, is often sufficient to identify specific important sample features such as low lifetime regions and high dislocation density regions.

3.) Using combinations of PL images taken under different experimental conditions, such as different illumination or detection wavelengths or both, one can eliminate the influence of doping variations, allowing direct correlation of intensity ratios with bulk material quantities such as bulk minority carrier lifetime or bulk diffusion length. While the use of different detection wavelengths (obtained with different spectral filters in front of the camera lens) has been disclosed in published PCT patent application No WO 2008/014537 A1, entitled 'Determining diffusion length of minority carriers using luminescence' and incorporated herein by reference, some specific and previously undisclosed advantages apply when this approach is applied to PL images taken on silicon bricks or ingots.

4.) The fact that PL images display the product of effective lifetime and background doping enables one to get information about relative or absolute variations of the background doping within the sample after normalising the measured PL signal for variations in the minority carrier lifetime. In specific cases an as-measured PL image reveals important information about doping variations without such normalisation.

5.) The dependence of bulk lifetime on injection level is simplified considerably for PL analysis of bulk silicon samples. PL images are typically measured with spatially constant illumination intensity, so different lifetime values within the same image taken on a silicon wafer are reported at different injection levels. The situation is surprisingly different for lifetime measurements taken on bulk silicon samples (such as bricks) under typical excitation conditions for PL imaging. Such measurements allow lifetime values within a considerable range to be measured in a single image taken with spatially constant illumination and at a well defined constant average injection level.

The PL techniques of the present invention have particular application to the characterisation of silicon bricks and ingots prior to wafering. Specific applications include determination of dislocation densities within a brick, acquisition of bulk lifetime images on the side facets of a brick, localisation and quantification of low lifetime regions within an ingot caused by high impurity concentrations, and measurement of the doping transition region in compensated or UMG silicon bricks or wafers. As will be explained in more detail below, manufacturers of bricks and wafers can for example use this information to improve the manufacturing conditions of ingots or as a cutting or sorting guide for ingots, bricks or wafers. The PL techniques can also be combined with infrared techniques (described above) to provide more complete information about structural and electronic properties of bricks. A new experimental system could combine PL imaging and infrared transmission in one tool that could be used either for off-line characterisation or sampling or for in-line characterisation of one or more surfaces of bricks during manufacturing.

Examples of how PL measurements can be used to improve the manufacturing conditions of ingots or as a cutting/sorting guide for bricks or wafers include the imaging of dislocation distributions, low lifetime regions, bulk lifetimes and compensated regions of UMG bricks, allowing defective regions to be discarded or manufacturing conditions to be improved. With reference to FIG. 2, fewer bricks may be produced if larger parts of the low lifetime regions 10 of an ingot are discarded during cutting, yielding a smaller number of bricks but the bricks will be of better quality.

FIG. 3 shows an example of a PL image on the side facet of a conventional cast p-type brick, revealing regions with high and low dislocation densities (dark regions 12 and bright regions 14 respectively), allowing estimation of the dislocation density within wafers that will be cut from that brick. Using PL images taken on more than one brick facet, a more reliable estimate of the dislocation density in subsequent wafers can be obtained. This analysis may be performed in combination with application of suitable image processing algorithms. One or several PL images on the side facets of a brick will provide information about the position of dislocation rich areas and may allow wafer manufacturers to sort wafers into quality bins (including a reject bin) simply based on information from PL images taken on the brick prior to wafering and on knowledge of the wafer position within the brick. The information may also provide a wafer manufacturer with rapid feedback on feedstock quality.

A PL image of a side facet of a UMG silicon brick is shown in FIG. 4. The dark band 16 visible near the top of the image (corresponding to a region near the top of the brick) represents the p-type to n-type transition region with effectively zero doping density. The PL image can thus be used to gain information quickly about the position of the transition region, allowing that part of the brick to be removed (since it cannot be used to manufacture solar cells) and separation of p-type wafers from n-type wafers. In combination with modelling, the position of the dark band in the PL image can also be used to calculate the ratio of doping atom concentrations in the feedstock, as described below.

Wafers that are cut from the bottom and top of a brick, and wafers that contain low lifetime regions around the edge as a result of impurities from the crucible walls, may produce lower efficiency solar cells. As shown in FIG. 3, low lifetime regions 10 appear dark in a PL image, so that one or several PL images on the side facets of a brick will provide information about the position of impurity-rich areas and may allow wafer manufacturers to sort wafers into quality bins (including a reject bin) simply based on the information from the PL images taken on the brick prior to wafering and on knowledge of the wafer position within the brick.

Wafer manufacturers can use bulk lifetime images on the side facets of bricks for more efficient and more reliable process monitoring and control than is possible with variations in uncalibrated or effective lifetimes. Bulk lifetime measurements obtained with any of the methods disclosed here can be used as an R&D tool for process optimisation and debugging. Bulk lifetime information obtained from measurements on the brick may also be used to sort wafers into different quality bins based on their position within the brick. Such binning may be based on the information obtained from one or more PL images taken on one or more side facets of the ingot The bulk lifetime information can also be used for fast feedback on feedstock quality.

The general concept of capturing PL images is described in the abovementioned published PCT patent application number WO 2007/041758 A1. The basis of PL imaging is that a substantial area of a sample is illuminated with light suitable for exciting photoluminescence from the sample, and the photoluminescence emitted from the illuminated area and/or from surrounding areas is imaged with a multi-pixel detector such as a silicon CCD camera. As such it is to be distinguished from the much slower PL mapping technique, described in U.S. Pat. No. 7,113,276 for example, where photoluminescence is generated by a focussed laser beam scanned point-by-point across a sample surface. It should be noted that the illuminated and imaged areas need not coincide; as disclosed in PCT patent application No PCT/AU2010/000577 entitled 'Material or device characterisation with non-homogeneous excitation' and incorporated herein by reference, it can be advantageous for example to illuminate one or more selected regions of a sample surface and image the photoluminescence emitted from nearby non-illuminated regions as well as from the illuminated regions.

PL imaging can be useful if one wants to observe the two-dimensional distribution of features such as dislocations or high impurity areas. However for large specimens such as silicon bricks or ingots it may be impractical if not impossible to obtain a single PL image of the area of interest, and it may therefore be necessary to stitch together two or more individual images to form a composite image. Such stitching may be necessary for example if the available light sources have insufficient power to illuminate the required area with sufficient intensity, or if higher spatial resolution than is possible with a single image is required. To acquire a composite image it is necessary to scan the sample and the illumination/detection system relative to each other. Possible scanning methods include: 'step and image', where a small area section is imaged and either the sample or the imager is moved onto the next section; 'scan and image', where the imager measures a fixed small area unit but is constantly in motion sweeping back and forth relative to the sample; or 'sweep imaging', where for example a line imager the full width of the sample is moved lengthwise relative to the sample. The stitching may be implemented in an automatic fashion using suitable image processing. When used in this specification, the terminology 'PL image' thus includes both single PL images and composite images generated from two or more individual images.

In other situations it may be unnecessary to obtain a two-dimensional PL image. For example if the quantity to be measured varies significantly in only one direction, such as the doping density in a silicon brick or ingot, a PL line scan will often be sufficient. A PL line scan can be acquired for example in a single frame with a line camera, or by scanning a point source across the sample surface in the required direction. There are also situations where a single PL measurement will suffice, for example to obtain an average measure of a quantity over a certain area. In this specification the inventive principles are primarily described with respect to PL area imaging, but it should be understood that they also apply to other forms of PL measurements, including line scans and single points.

1) Determination of Bulk Lifetime in Bricks and Ingots from PL Imaging

Bulk lifetime images of bricks and ingots are obtained from PL images in the following sequence:

(i) Measure a PL image;

(ii) Convert the measured PL count rate (or intensity) in each pixel into a normalised count rate (or intensity) $PL_{norm}$ that is normalised with regard to spatial background doping density variations and optionally also with regard to variations in measurement parameters such as exposure time, pixel binning (i.e. the number of pixels binned in the X-direction multiplied by the number of pixels binned in the Y-direction), incident light intensity and collection optics efficiency;

(iii) Convert the resulting normalised image into an absolute bulk lifetime image using a predetermined theoretical or empirical relationship.

Step (i) has been described in the abovementioned published PCT patent application number WO 2007/041758 A1, and includes the possibility of creating a composite FL image by stitching together two or more images taken on different parts of the same sample surface.

Step (ii) can be performed with experimental data for the background doping density or, if the background doping density is sufficiently predictable in production, based on theoretical or empirical data. In singly doped silicon (i.e. p-type or n-type silicon that contains one dominant type of doping atom), the background doping density can be obtained from resistivity measurements using tabulated data for the mobilities of electrons and holes for the conversion of resistivity into doping density. The resistivity can be measured by several methods including contact measurements (four point probe) and non-contact measurements (e.g. inductive coil, Eddy current, surface voltage). These techniques (among others) can provide spatially resolved information about the doping density when performed in a scanning mode or by using more than one sensor located in different positions, or by a combination thereof. To reduce the measurement time, a two dimensional distribution of the doping density may be measured with coarse spatial resolution, which is then used to normalise the PL image after suitable interpolation or extrapolation of the data. Coarse spatial information about the background doping density is sufficient in many practical cases since long range resistivity variations are more typical than small scale/short range variations.

Alternatively, in the case of side facets of ingots or bricks, one or more line-scans of the doping density from top to bottom may be sufficient, since the strongest relative variations occur predominantly in only one direction, e.g. from bottom to the top of an ingot or brick.

In another alternative the measured doping density variation may be fitted with an expected theoretical relationship (e.g. the Scheil equation) and the doping variation across the entire sample area then calculated for each pixel from that equation. The experimental data that form the basis of the fitting can be a two-dimensional map or one or more line scans or even just one or more single measurement points across the surface. The influence on the analysis of noise in the doping density data, unavoidable in experimental data, is thereby avoided. In addition, some measurement techniques such as the Eddy current technique generate artefacts in the measured resistivity near the edges of samples. In such cases the experimental data would require correction of these artefacts or extrapolation of the data from regions unaffected by the artefacts. Some fitting and extrapolation routines are therefore required in any case.

In yet another alternative, no measurement of the doping is performed at all, and the variation of the doping density is determined solely from a theoretical relationship or from statistical/empirical production data.

Whatever experimental or theoretical method is used to determine the doping density, that information, along with the measurement time, pixel binning settings and variations (experimentally measured or modelled) in the incident illumination intensity and collection optics efficiency if required for improved accuracy, is used to convert the measured PL data into $PL_{norm}$. The resulting normalised PL data is indicative of relative variations in effective minority carrier lifetime across the image area.

Step (iii), the conversion of the normalised PL intensity $PL_{norm}$ into bulk lifetime $\tau_{bulk}$ can be performed based on an empirically determined relationship $PL_{norm}=f_{empirical}(\tau_{bulk})$ that can be obtained by calibrating experimental normalised PL data from one or more samples against bulk lifetime data obtained on those same samples by some other means. Techniques (such as QSSPC) for measuring the effective lifetime, with known relation between bulk and effective lifetimes, may be applied to obtain the bulk lifetime data. These other measurement techniques may be performed on a calibration sample after surface passivation for more reliable results. Alternatively, a calibrated PL image taken on a passivated sample may be used as the reference bulk lifetime data for the determination of the empirical relationship. As discussed above the injection level has an important impact on the bulk lifetime, so that calibration of PL data versus any other technique needs to be performed with both measurements at the same or similar injection level.

Apart from the bulk lifetime and the doping density, the main variables affecting the detected PL intensity from an unpassivated silicon brick are the surface properties of the sample, specifically the surface texture, reflectance and depth and severity of sawing-induced surface damage. In practice the same empirical relationship $PL_{norm}=f_{empirical}(\tau_{bulk})$ may be used for bricks/ingots at the same stage in a production line, since the surface properties can be expected to be sufficiently similar. However separate empirical relationships may have to be determined for ingots/bricks at different production stages (e.g. polished bricks versus as-cut unpolished bricks). In production the calibration correlation $PL_{norm}=f_{empirical}(\tau_{bulk})$ for samples at a specific processing stage may have to be checked and updated on a regular basis.

Figure 5B:
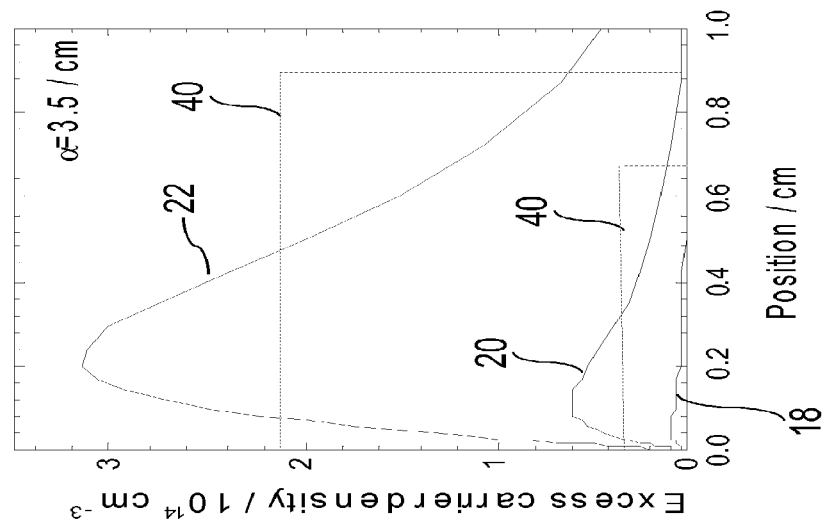
FIGS. 5(a) and 5(b) show excess carrier density profiles calculated for a 15 cm thick silicon brick for two different excitation wavelengths (indicated by the different absorption coefficients) and for different values of the bulk lifetime.
Figure 5A:
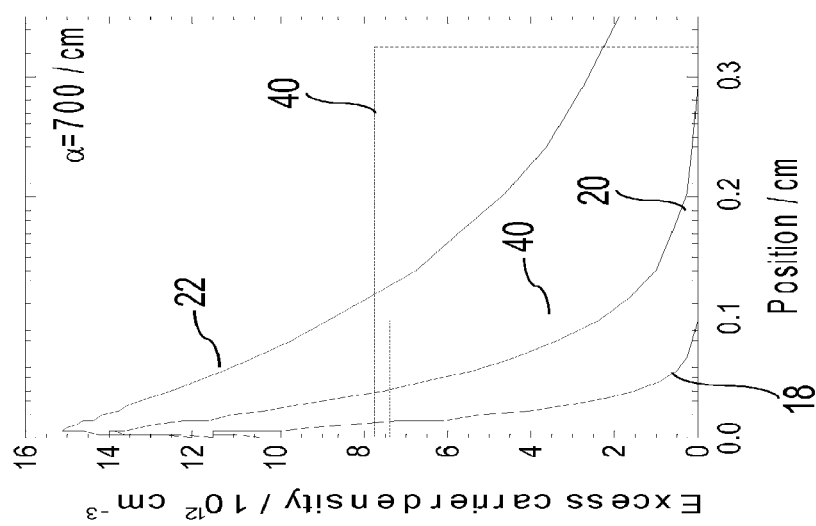

Conversion of the normalised PL intensity into bulk lifetime can also be performed based on a predetermined theoretical relationship $PL_{norm}=f_{empirical}(\tau_{bulk})$ Calculation of this relationship is based on analytically or numerically calculating the depth-dependent minority carrier density $\Delta n(y)$ within the sample for given illumination conditions, where y is the distance from the surface. FIGS. 5(a) and 5(b) show carrier profiles in a 15 cm thick silicon brick for two different absorption coefficients of the excitation light (implying different excitation wavelengths). In each graph the depth dependent carrier density is shown for three values of the bulk minority carrier lifetime: $\tau_{bulk}$=10 μs (plot 18); $\tau_{bulk}$=100 μs (plot 20); and $\tau_{bulk}$=1000 μs (plot 22). Such calculations can be performed using analytical models for the excess carrier density or numerical modelling packages such as DESSIS or PC1D. The detected PL rate can then be calculated by integrating the rate of spontaneous emission over the thickness of the sample and over the emission spectrum, taking into account re-absorption within the sample, the sensitivity of the detector and the transmission of filters, as described for example in T. Trupke, 'Influence of photon reabsorption on quasi-steady-state photoluminescence measurements on crystalline silicon', *Journal of Applied Physics* 100, 063531 (2006). Performing these calculations for a range of different bulk lifetime values allows one to calculate the theoretical relationship $PL_{norm}=f_{empirical}(\tau_{bulk})$.

Calculations as described above can in principle provide a quantitative relationship between the normalised PL count rate (indicative of the effective lifetime) and the bulk lifetime. In practice however, these calculations generally provide only a relative relationship $PL_{norm}=C^*f_{theoretical}(\tau_{bulk})$, because of uncertainties in assumptions that have to be made about various hardware parameters and sample properties. The scaling factor C will be constant or very similar for different samples (bricks) at the same processing stage, but may have to be determined separately for bricks at different processing stages. In principle therefore, for measurements on bricks in production at the same processing stage (e.g. after polishing), calibration of a measurement system only needs to be performed once for a specific hardware system, although in practice the calibration could be repeated at regular intervals to monitor and compensate for drifts of hardware components for example. The determination of C is performed in a similar way as described above, by comparison with actual bulk lifetime data determined from some other technique. Alternatively C may be determined by comparison with another calibrated PL imaging system. A single data point is sufficient for that calibration, but for more reliable results the average of two or more data points from one or more samples may be used. For example the calibration constant may be determined by comparison of cross sections or histograms of bulk lifetime taken on one or more facets of silicon bricks.

The self-consistent measurement techniques described below that determine bulk lifetime from combinations of images taken under different conditions may also be used to calibrate the system.

Figure 6:
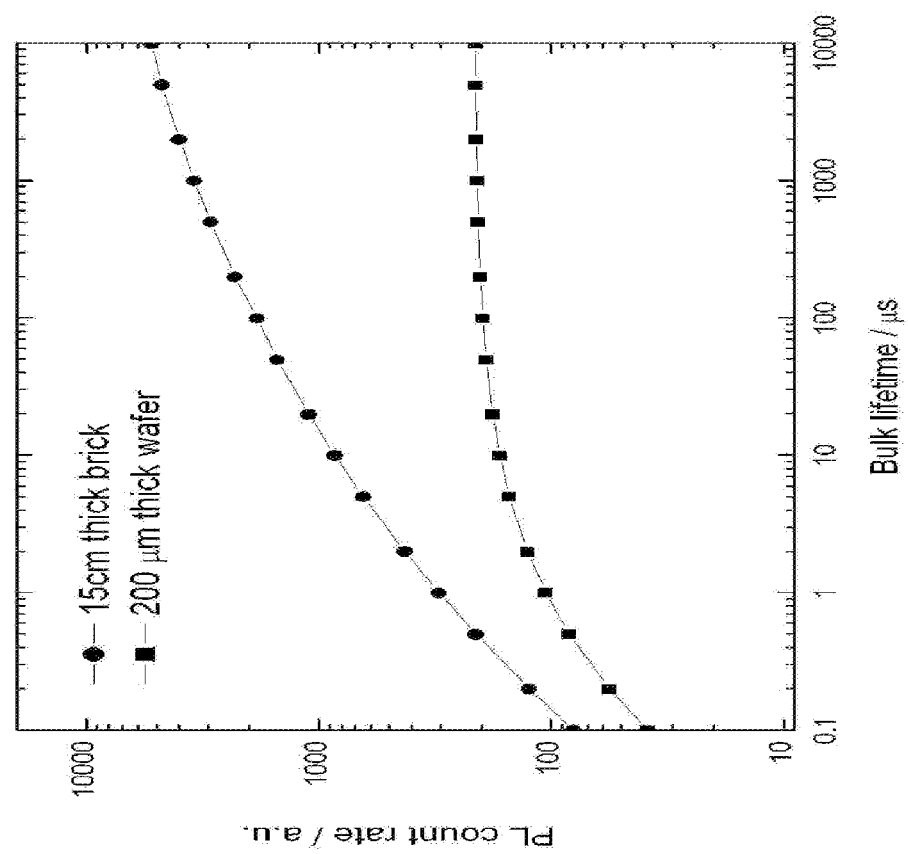
FIG. 6 shows theoretical relationships between normalised PL count rate and bulk minority carrier lifetime for a 15 cm thick silicon brick (circles) and a 200 μm thick silicon wafer (squares)

FIG. 6 shows example theoretical relationships between normalised PL count rate (indicative of effective lifetime) and bulk lifetime that were calculated as described above, for an unpassivated 15 cm thick silicon brick (circles) and for an unpassivated 200 μm thick silicon wafer (squares). These relationships are highly non-linear, and inspection of the two curves highlights an unexpected benefit of PL measurements on bulk samples such as bricks or ingots, compared to thinner samples such as unpassivated wafers. For the unpassivated wafer the normalised PL count rate saturates for bulk lifetime values larger than $\tau_{bulk}$~10 μs, whereas for the brick it continues to vary significantly at much higher bulk lifetime values, with no saturation for bulk lifetime values of up to ten milliseconds. The saturation observed in the wafer is caused by the diffusion length becoming larger than the thickness for bulk lifetimes greater than ~10 μs, in which case further increasing the bulk lifetime or bulk diffusion length does not increase the total carrier density in the sample. A common description of this phenomenon is that the effective carrier lifetime becomes limited by the surfaces. In contrast, for the much thicker brick sample the diffusion length remains small compared to the thickness, so that the carrier density within the brick keeps increasing with the diffusion length and does not become surface limited. An important consequence of this is that in principle PL signals obtained from unpassivated bricks can be reliably converted into bulk lifetime or bulk diffusion length data over a much wider range of bulk lifetime values than is possible for unpassivated wafers.

Calculations of normalised PL intensity as a function of bulk lifetime (such as those shown in FIG. 6) show that the actual shape of the curve depends on the spectral sensitivity of the apparatus used to measure the PL, which is generally determined by the spectral sensitivity of the camera and the transmission of filters in front of the camera. Enhancing the spectral sensitivity at longer wavelengths causes a stronger (steeper) dependence of the normalised PL signal on bulk lifetime, allowing a more accurate conversion of PL intensity into bulk lifetime. This effect is visible in the graphs shown in FIG. 7, which compare the expected variation in PL signal from a selected region of a 15 cm thick silicon sample as a function of bulk lifetime for two different detection wavelength intervals, 950-1000 nm (squares) and >1050 nm (circles). The higher sensitivity of the PL signal at longer wavelengths arises because longer wavelengths probe the carrier density deeper inside the sample (e.g. a brick), where most of the variation of the excess carrier density occurs for long bulk lifetimes (compare FIG. 5(b)). In practice this long wavelength sensitivity enhancement may be achieved either by enhancing the relative long wavelength sensitivity by introducing into the detection system long pass filters with cut-on wavelength in the 1000-1200 nm range, or by enhancing the absolute long wavelength sensitivity by using a detector that is more sensitive at longer wavelengths, for example an InGaAs camera instead of a silicon camera.

An example of the conversion of a raw PL image to a bulk lifetime image will now be explained, with reference to FIGS. 8(a) to 8(e). FIG. 8(a) shows a PL image 24 acquired from the side facet of a p-type silicon brick, and FIG. 8(b) shows a representative distribution 26 of the p-type dopant (boron) across the side facet, the greyscale representing the dopant concentration. The dopant distribution was calculated from the Scheil equation, with the maximum dopant concentration 28 at the top of the brick. Bearing in mind that the intensity variation in a PL image is determined by the product of the doping concentration and the effective minority carrier lifetime, the PL image of FIG. 8(a) is normalised by the dopant distribution of FIG. 8(b) to yield the normalised PL image 30 shown in FIG. 8(c). Intensity variations in FIG. 8(c) are indicative of variations in effective minority carrier lifetime. To convert effective lifetime to bulk lifetime, the normalised PL image 30 is corrected using the representative non-linear relationship between effective lifetime and bulk lifetime shown in Hg 8(d) to produce the bulk lifetime image 32 of FIG. 8(e), showing variation of bulk lifetime across the side facet of the sample brick. Note that in this illustrative example, the particular non-linear relationship in FIG. 8(d) is a simple cubic equation, used to represent an actual empirical or theoretical relationship of the type shown by the filled circles in FIG. 6.

2) Interpretation of Relative Intensity Variations in PL Images on Bricks/Ingots Step ii) in the above example application, i.e. the normalisation of PL count rate with regard to background doping density and optionally variations in measurement parameters, may not be required for some specific applications, where absolute count rates are of secondary concern and where PL images are analysed in terms of specific patterns or relative variations. Two examples are the identification of regions with high dislocation density (as shown in FIG. 3 for example) and the identification of low lifetime regions at the top, the bottom and the side walls of a brick or ingot (as shown in FIGS. 2 and 3 for example). Image processing algorithms may be applied to distinguish such features within the images from other features in the image.

The dislocation density observed in PL images of side facets of bricks may be used to estimate the dislocation density in wafers cut from that brick, and to estimate the volume density of dislocations within the brick as a function of height within the brick. That information may be used for quality binning and sorting of wafers. These estimates will become more accurate by combining the information from PL images taken on more than one, up to four side facets of the brick.

Similarly, a PL image on a side facet of a brick can be used to identify the position and expanse of low lifetime regions at the top, bottom, and in some cases the side walls. Again, such analyses will be more accurate if PL images of more than one, up to all four side facets are combined. PL images taken on the brick may be also used to predict the lifetime distribution in wafers cut from that brick; for example the low lifetime region 10 (dark area) on the right hand side of the image shown in FIG. 3 will result in a low lifetime region near the edge of wafers sliced from that portion of the brick. PL images of the side facets of ingots may also be used to guide the cutting of the ingots into bricks.

3) Combining Images Taken Under Different Measurement Conditions (a) Different Detection Wavelengths In the abovementioned published PCT patent application number WO 2008/014537 A1 we described a technique whereby at least two luminescence images are taken with different spectral filters mounted in front of the camera lens. Since long wavelength luminescence has a higher average optical path length within the sample before re-absorption, measurements with different filters in front of the detection system allow capture of luminescence emitted from different depths in the sample. It was shown that the ratio of luminescence intensities measured with two different filters can be converted into bulk diffusion length. Compared to electroluminescence (EL) images on finished solar cells, it has been shown that this approach has the advantage that local variations of the diode voltage, normally present during EL imaging on cells, cancel out in the luminescence intensity ratio so that the intensity ratio of two uncalibrated images provides the diffusion length in absolute units.

The basis for this method is that the relative carrier density profile across the thickness of a sample changes with the diffusion length, but this method becomes insensitive to variations in diffusion length once the diffusion length is a few times larger than the sample thickness. The same argument applies in the context of applying a similar technique to bricks that are typically >10 cm thick, however now the condition of the diffusion length being smaller than the sample thickness is fulfilled over a much wider range of values, more specifically for all practical values of interest for silicon. Variations of the bulk lifetime or the bulk diffusion length thus have an influence on luminescence intensity ratios over a much wider range of bulk lifetime or bulk diffusion length values in bricks than is the case for wafers or cells.

Applying the above method of calculating intensity ratios of images taken with identical excitation but variable detection conditions has two benefits: firstly, variations of the background doping across a brick are eliminated from a PL intensity ratio; and secondly the ratio of two uncalibrated PL images, each in relative units (each measured with the same incident light intensity and each normalised for the camera exposure time and binning) provides the absolute bulk lifetime or bulk diffusion length without a need for external calibration.

This method may be applied as follows:

Step (i): measure two PL images with the same or similar illumination intensity but with two different wavelength detection bands. Preferably one measurement should be of short wavelength photons, to yield enhanced information about the carrier density near the front surface, whereas the second measures longer wavelength photons, thereby measuring the average carrier density up to a specific depth of the sample.

Step (ii): optionally normalise each image with regard to the camera exposure time and binning, and if necessary with regard to experimentally measured or modelled variations in the illumination intensity and/or the efficiency of the collection optics.

Step (iii): for each pixel calculate the intensity ratio from the two normalised images.

Step (iv): for each pixel convert the calculated intensity ratio into bulk lifetime using a predetermined relationship.

Alternatively, a combined normalisation for variations in the illumination intensity and/or the efficiency of the collection optics can be applied to the intensity ratio, rather than to the individual images. The predetermined relationship from step (iv) can be determined empirically by comparison of experimental PL intensity ratios with experimental bulk lifetime or bulk diffusion length data, or obtained theoretically by calculating relative carrier profiles for a range of different bulk lifetime/diffusion length values analytically or numerically with a common modelling program (e.g. DESSIS, PC1D), then using the carrier profiles to calculate the two expected measured PL intensities for each bulk lifetime/diffusion length value, taking into account re-absorption and the spectral sensitivity of the sensor. These calculations are performed separately for the two PL images. The expected PL intensity ratio is calculated for each bulk lifetime/diffusion length, and an analytical curve or lookup table is generated for the intensity ratio as a function of bulk lifetime/diffusion length.

Figure 7:
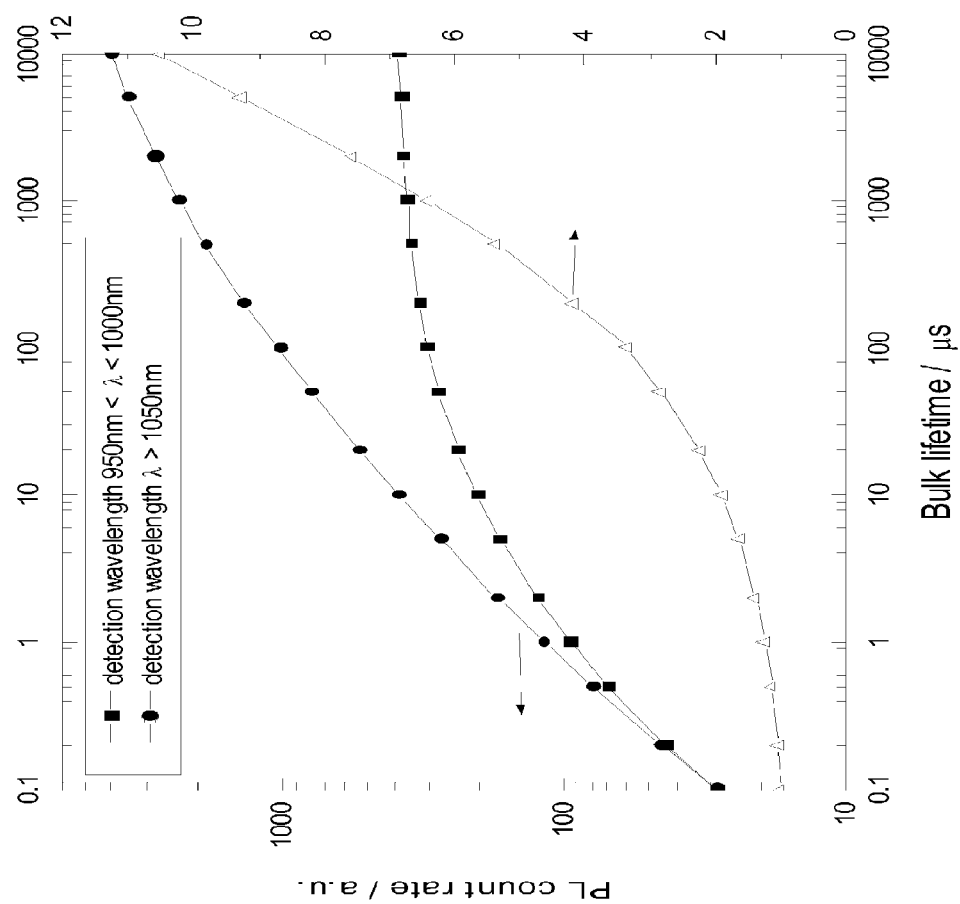
FIG. 7 shows plots of detected PL intensity versus bulk lifetime for a 15 cm thick silicon brick, for PL measured in two different spectral regions, as well as the intensity ratio.

FIG. 7 shows calculated data for the detected PL intensity as a function of bulk lifetime in a 15 cm thick silicon sample. Referring to the left hand Y-axis, the theoretical PL intensity acquired with a 950-1000 nm spectral range is plotted as filled squares, while the theoretical PL intensity acquired with >1050 nm is plotted as filled circles. Referring to the right hand Y-axis, FIG. 7 also shows the ratio of the two PL signals as a function of bulk lifetime (open triangles), and it can be seen that the variation in the intensity ratio allows direct correlation with the bulk lifetime. The fact that the two filter combinations yield the same PL count rate at low bulk lifetime values, resulting in unity intensity ratio, is a coincidence resulting from this specific choice of wavelength intervals and the specific experimental conditions modelled.

If an InGaAs camera, an IR sensitised photoelectron multiplication silicon camera or similar sensor with significant spectral sensitivity in the 1100-1300 nm range were used with appropriate longer wavelength filters, one could detect variations of the carrier density deeper inside the brick, thereby enabling the detection of diffusion length variations in a regime of still higher diffusion lengths.

The intensity ratio curve in FIG. 7 shows that the variations in the intensity ratio are strongest at high bulk lifetime values, so that the method may be particularly useful for measurements on the side facets of monocrystalline ingots or bricks or the surfaces of high lifetime multicrystalline bricks.

Dielectric filters are in principle well suited to the selection of different PL wavelength bands, because of their sharp cut-on or cut-off wavelength i.e. the transition from high to low transmission. However the transmission of dielectric filters has a strong angular dependence, whereby the cut-on/cut-off wavelength moves to shorter wavelengths with increasing angle of incidence. This effect needs to be considered in the present application where, as shown in FIG. 11, PL emission 40 from an extended sample 42 such as a silicon wafer or brick impinges on a dielectric filter 44 placed in front of the imaging camera 46 at a range of incidence angles. Clearly this will affect the PL intensity distribution within individual PL images, and therefore the intensity ratio and the analysis result. The effect will be even more pronounced if a dielectric long pass (LP) filter is used to obtain the longer wavelength PL image and a dielectric short pass (SP) filter is used to obtain the shorter wavelength PL image, because the angular dependence of the cut-on/cut-off wavelength has opposite effects on images acquired through LP and SP filters. To explain, the shift in the cut-on/cut-off wavelength to shorter wavelengths with increasing angle of incidence means that a PL image acquired through an SP filter will have relatively reduced intensity in the off-axis portions, while a PL image acquired through an LP filter will have relatively increased intensity in the off-axis portions.

There are a number of means for mitigating this problem that may be applied individually or in combination. Inspection of FIG. 11 shows that increasing the distance between the camera 46 (and the filter 44) and the sample 42 will reduce the range of incidence angles, within the constraints of system design and the inevitable reduction in received signal strength because of the approximately Lambertian pattern of PL emission from the sample surface.

Another method is to apply suitable corrections to the long and short wavelength images, using flat field corrections measured for each filter to take into account the angular dependence of their transmission. A flat field correction for a given filter may for example be obtained by acquiring through the filter a PL image of a high quality monocrystalline silicon wafer that can be expected to have uniform PL response across its area. The flat field correction thus derived will also correct for other non-uniformities in the system, in particular the angular dependence of the efficiency of the collection optics. Because dielectric filters may not be homogeneous across their area, it may also be necessary to measure the flat field correction for a specific filter orientation, and to maintain that orientation during subsequent acquisition of images. When calculating an intensity ratio of two images with different filters, one can either correct each image before calculating the ratio, or correct the intensity ratio image using a combined flat field correction.

Figure 13A:
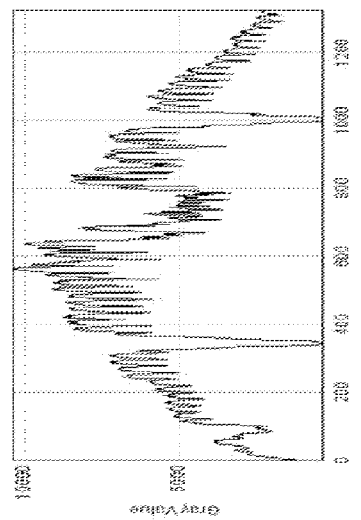
FIGS. 12(a) to 12(d) and 13(a) to 13(d) illustrate the correction of a PL intensity ratio image for the dependence of dielectric filter transmission on incidence angle.
Figure 13B:
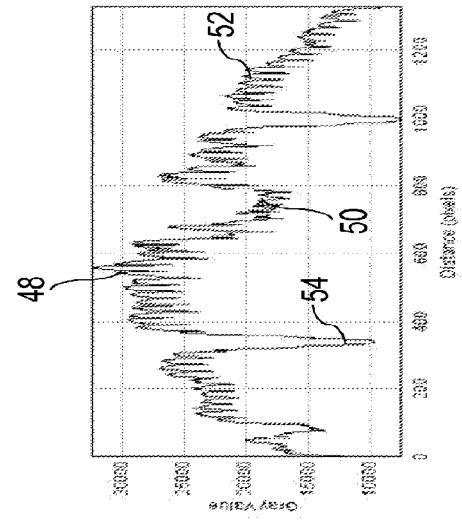
Figure 12A:
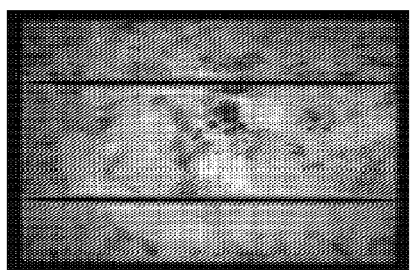
Figure 12B:
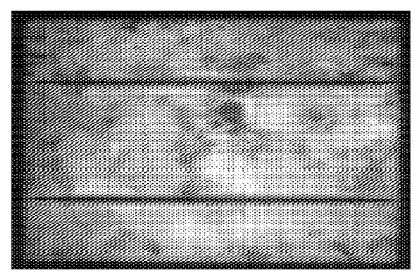
Figure 13C:
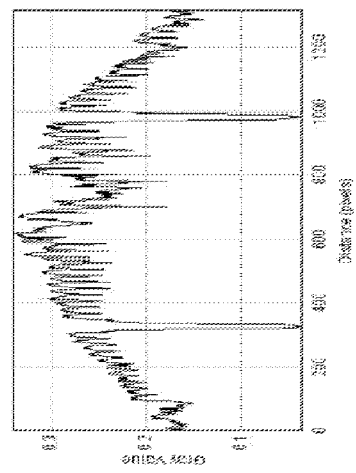
Figure 13D:
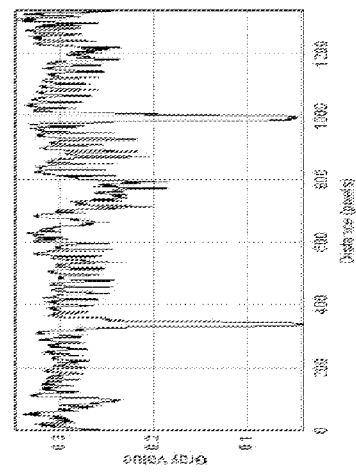
Figure 12C:
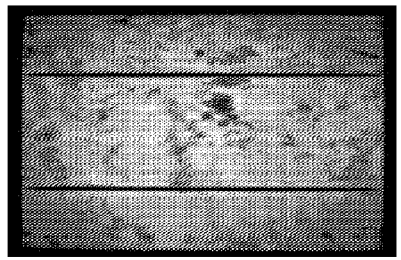
Figure 12D:
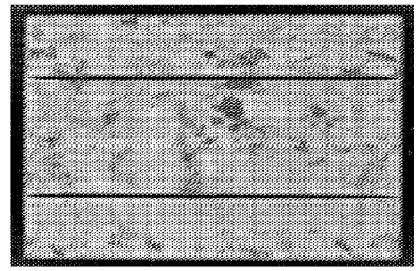

To illustrate this correction procedure, FIGS. 12(a) and 12(b) show PL images of a silicon solar cell acquired with a silicon CCD array through a 1000 nm SP filter and a 1050 nm LP filter respectively. FIG. 13(a) shows a profile of the PL intensity along a diagonal cross section of the FIG. 12(a) image, while FIG. 13(b) shows the corresponding profile for the FIG. 12(b) image. The intensity profiles show high intensity regions 48 and low intensity regions 50 superimposed on a comb-like pattern 52 caused by the metal fingers, and low intensity spikes 54 caused by the bus bars. It will be seen that the intensity of the FIG. 12(a) (SP) image is significantly reduced in the corners, which is partly due to the filter angular dependence described above. We note that the intensity of the FIG. 12(b) (LP) image is also reduced in the corners, although to a lesser extent than for the SP image; this is because the effect of the filter angular dependence, which tends to increase the intensity in the corners, is outweighed by other effects such as the angular dependence of the collection optics. The image shown in FIG. 12(c) is an intensity ratio of the images shown in FIGS. 12(a) and 12(b), and FIG. 13(c) shows the PL intensity profile along a diagonal cross section, again showing a roll-off in the corners. Finally, FIGS. 12(d) and 13(d) show the flat field corrected intensity ratio image and its corresponding PL intensity profile, and it is clear that the angular dependence artefact has been removed.

Alternatively, absorption filters could be used to select the different wavelength PL bands. Unlike dielectric filters their transmission has little dependence on the angle of incidence, however their absorption edges are less steep resulting in inferior band selection/rejection.

We note that the FIG. 12(b) image, of longer wavelength PL emission, is more blurred than the FIG. 12(a) image. This is because of the lower absorption of longer wavelength light in silicon, leading to lateral smearing within the pixels of the silicon CCD camera. As discussed in published PCT patent application No WO 09/121133, image contrast in this circumstance can be enhanced by applying a theoretical or experimentally measured point spread function for the optical detection system.

Figure 14A:
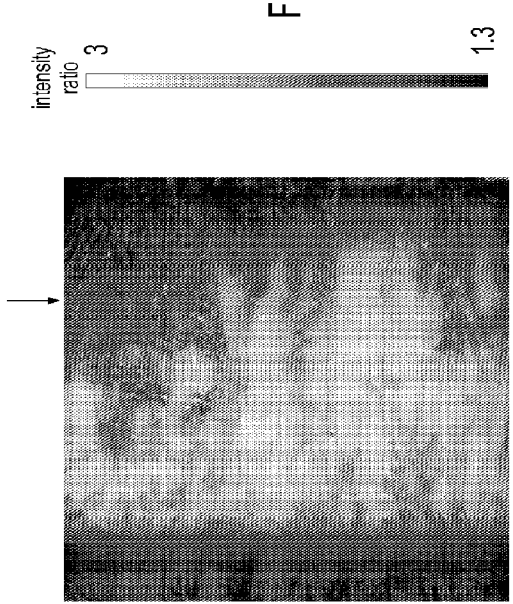
FIGS. 14(a) and 14(b) illustrate the conversion of an intensity ratio image for PL measured in two different spectral regions (FIG. 14(a)) to a bulk lifetime image (FIG. 14(b)).
Figure 14B:
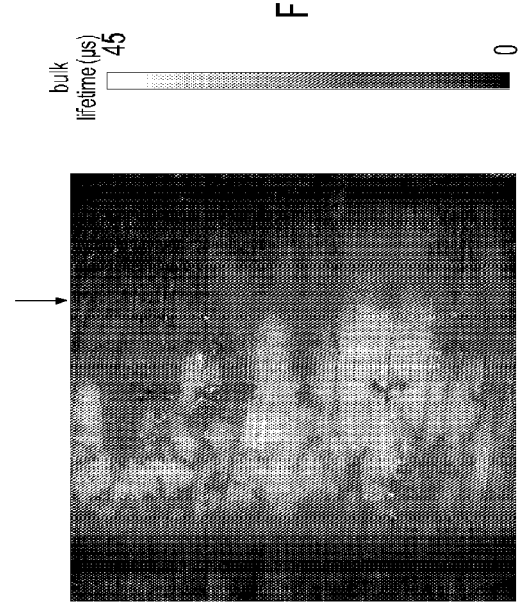

An actual implementation of the intensity ratio method is illustrated in FIGS. 14(a) and 14(b). One side of a p-type multicrystalline silicon brick was illuminated with ~1 Sun of near IR light from a diode laser array and the PL emission imaged by a Si CCD camera firstly through a 1050 nm LP filter and secondly through a 1000 nm SP filter. The intensity ratio of the images was calculated pixel by pixel, and the resulting ratio image is shown in FIG. 14(a), where the ratio ranges from 1 in low lifetime regions to 3 in high lifetime regions. For each pixel, the intensity ratio was then converted into bulk lifetime using a theoretical relationship, with the resulting bulk lifetime image shown in FIG. 14(b). We note that because of the size of the brick it was necessary to acquire two images with each filter and stitch them together; the joins in FIGS. 14(a) and 14(b) are indicated by arrows.

It will be appreciated that using an optical filter to select the wavelength range of the PL decreases the intensity of the PL signal at the camera, potentially increasing the image acquisition time and slowing the method down. In a variant embodiment, the short wavelength and long wavelength PL images are acquired with reduced spatial resolution, but without compromising the signal to noise ratio, using pixel binning, and the two images processed as described previously to obtain a reduced spatial resolution image of the bulk lifetime. A higher resolution PL image, i.e. without pixel binning, is then acquired without optical filtering, and the data correlated to obtain a higher resolution image of the bulk lifetime. This embodiment requires the acquisition of a third PL image, but may be faster because the filtered images can be acquired more rapidly. Comparison of the bulk lifetime data obtained from the intensity ratio image with an unfiltered PL image can also be used to obtain information on the background doping variation within the sample.

(b) Different Excitation Wavelengths

Figure 9:
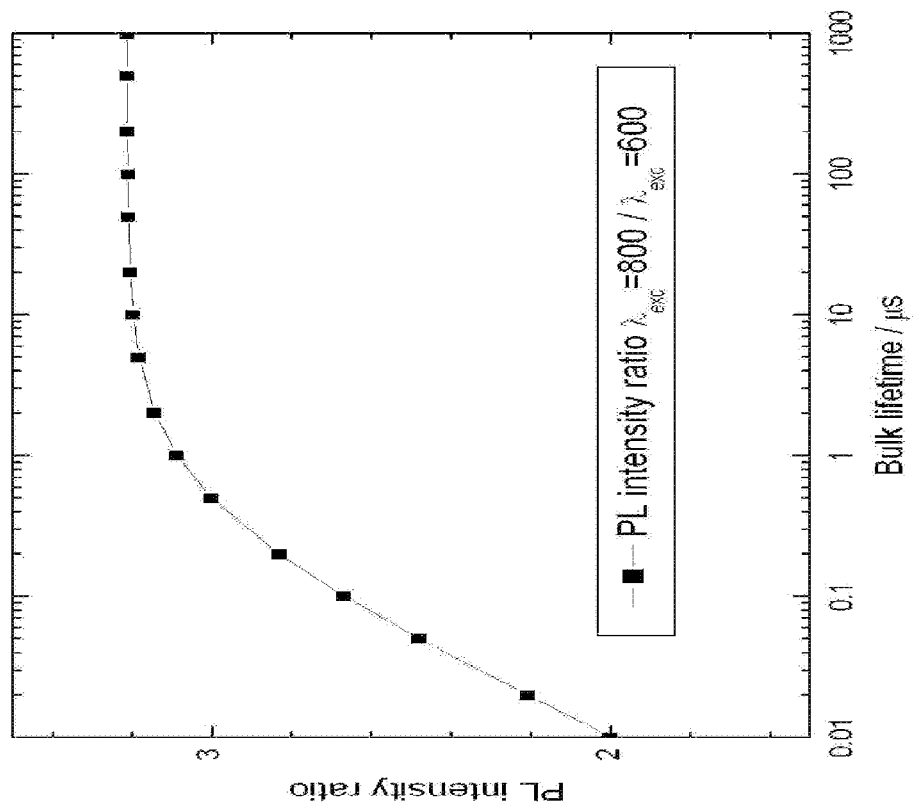
FIG. 9 shows a plot of intensity ratio versus bulk lifetime for PL generated from a 15 cm thick silicon brick by two different excitation wavelengths.

In a similar fashion, absolute lifetime/diffusion length distributions can be obtained from the ratio of PL images taken on bricks or ingots with identical detection wavelength bands but with different excitation wavelengths that create excess carriers at different depths within the sample. FIG. 9 shows the luminescence intensity ratio between two PL images obtained from a 15 cm thick silicon brick with 800 nm excitation and 600 nm excitation, as a function of the bulk lifetime.

The intensity ratio curve shown in FIG. 9 shows that this approach provides absolute lifetime or diffusion length information only for short diffusion lengths/lifetimes since the ratio of PL intensities taken with different excitation wavelengths is largely insensitive to bulk lifetime variations for values larger than 10 μs. For longer diffusion lengths the excitation wavelength has no significant impact on the relative carrier density profile so that the PL intensity ratio becomes constant. However some of the same benefits as for measurements with variation of the detection wavelength range still apply, in that variations of the background doping across a sample are eliminated from a PL intensity ratio, and the ratio of two uncalibrated PL images, each in relative units (each measured with the same incident light intensity and normalised for the camera exposure time and binning) provides the absolute bulk lifetime or bulk diffusion length without a need for external calibration.

(c) Different Detection and Excitation Wavelengths

It is also possible to determine the bulk properties of a sample by taking the intensity ratio of two PL images in which both the excitation and detection wavelengths are varied between the two images. Alternatively the two approaches may be combined so that the intensity ratio of two images taken with different detection wavelengths is analysed in regions with high bulk lifetime, while the ratio of images taken with different excitation wavelengths is analysed in regions with low bulk lifetime.

4) Obtaining Information about Variations in the Background Doping

The following applications are particularly useful for bricks and ingots but could in principle also be applied to wafers with lateral variations of the doping density. Since the measured PL signal is proportional to both the effective lifetime and the background doping density, information about the background doping density can be obtained by normalising the measured PL intensity with regard to lifetime variations measured in a separate lifetime measurement. Specifically, the methods described in section 3) above allow one to obtain the bulk lifetime without the need for calibration.

From any bulk lifetime variation data the expected normalised PL intensity variation can then be calculated from the relationship between normalised PL count rate and bulk lifetime as shown in FIG. 6. The ratio between a measured PL image and the PL intensities expected according to the bulk lifetime will then give the relative doping density variation across the sample. Specifically, this approach may be applied using bulk lifetime data obtained from the methods described in section 3) above. In this case the PL image can be one of the two individual PL images taken with either different detection wavelength ranges or different illumination wavelengths, or a third PL image. Alternatively, in cases where a separate measurement of the effective lifetime is performed, a PL image that is normalised with regard to effective lifetime variations then represents an image of the relative doping density variation. Either way, the relative doping density variation across the sample can be calibrated into an absolute doping density image if either the doping density at one point or the average doping density of the sample is known. When applied to samples with similar surface properties in production the above calibration into absolute doping density may not be necessary on every sample. Instead, the same calibration constant may be applied to different samples with similar or substantially identical optical surface properties (such as polished bricks).

In cases where the effective lifetime can be assumed to be constant, the as-measured PL intensity variation represents an image of the relative doping density variation, which again can be calibrated into an absolute doping density image if the doping density in one point or the average doping density of the sample is known. An example of a sample type where this assumption holds is unpassivated wafers with high bulk lifetime; in these samples the effective lifetime (compare squares in FIG. 6) is constant and the PL intensity directly reveals doping variations. This can be used for example to measure doping striations in monocrystalline wafers.

In other specific cases the doping density variations are so dramatic that small variations in the effective lifetime only cause a small error that may be insignificant for some applications. One such special case concerns compensated or UMG bricks, where in the transition region from p-type to n-type the changes in the effective doping density are very pronounced, revealed in a deep minimum in the PL count rate. For example in the PL image of a UMG brick shown in FIG. 4 the dark band 16 near the top shows the exact position of the transition region, without the need to compensate the PL signal for lifetime variations. The ability to locate the transition region quickly and accurately provides wafer manufacturers with a cutting guide to identify and sort wafers from the p-type, transition and n-type regions. The analysis discussed below is also performed without taking into account variations in the lifetime; it is thus assumed that effective lifetime variations are much smaller than the variations in effective doping density.

Figure 10:
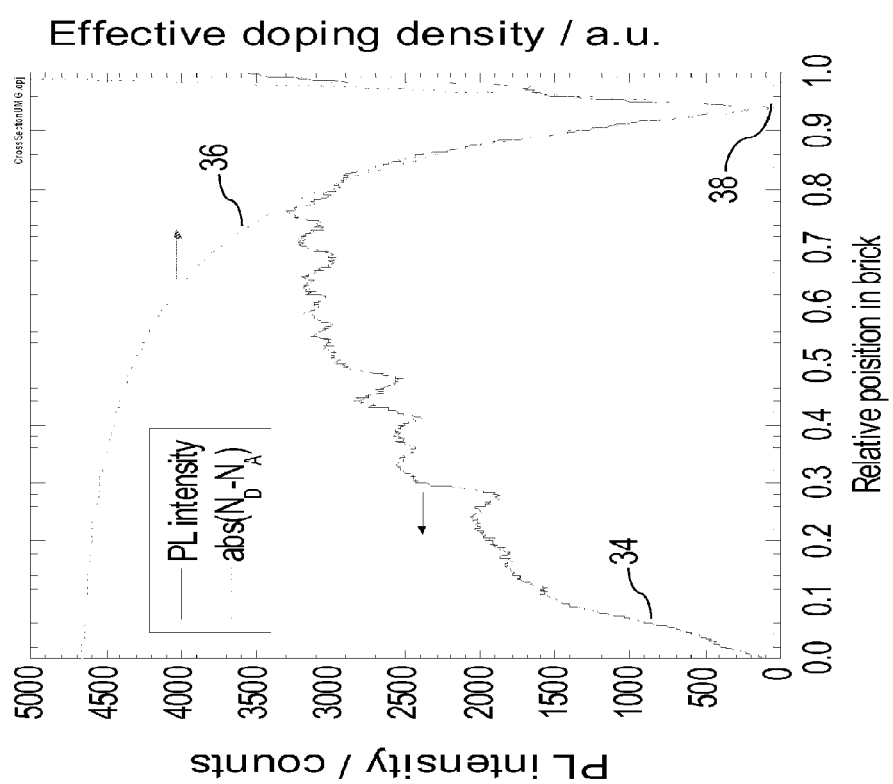
FIG. 10 shows a line scan of the PL intensity from bottom to top of the brick shown in FIG. 4, as well as the calculated effective doping density.

To illustrate the direct conversion of PL data to doping density variations, FIG. 10 shows (with reference to the left hand Y-axis) a line scan 34 from bottom to top (left to right) of the PL intensity in the PL image shown in FIG. 4, and (with reference to the right hand Y-axis) the fitted theoretical effective doping density, i.e. the absolute value of the difference between the boron and phosphorous concentrations (dotted line 36), each calculated separately according to the Scheil equation. In the absence of variations in effective lifetime, the PL intensity is expected to be proportional to that effective doping density.

In calculating the theoretical effective doping density, the segregation coefficients $k_{eff}$ for boron and phosphorous in crystalline silicon were taken from the literature. The only remaining fitting parameters were the initial concentrations of boron and phosphorus in the feedstock, $N_B(0)$ and $N_P(0)$; these parameters were varied to achieve the best fit between the effective doping in relative units 36 and the as-measured PL intensity line scan 34. Variation of $N_B(0)$ and $N_P(0)$ results in variations in the absolute effective doping and a shift on the X-axis of the minimum in effective doping, and these parameters were varied until the minimum coincided with the minimum of the PL intensity 38.

Fitting of the relative effective doping density to the PL intensity cross section, as shown in FIG. 10, thus allows quantification of the ratio $N_B(0)/N_B(0)$. This approach is based on the assumption that the feedstock contains only one major donor species and one major acceptor species, and that both donor and acceptor atoms are distributed in accordance with the Scheil equation. Under these assumptions the approach would work in a similar fashion for other doping atoms in silicon, such as gallium.

5) Influence of Injection Level on Minority Carrier Lifetime

It will be recalled from the Background section that under quasi steady state conditions the effective minority carrier lifetime is inversely proportional to the generation rate G and proportional to the minority carrier density, so that $\tau_{eff}=\Delta n/G$. However the fact that minority carrier lifetime is also a function of injection level complicates known lifetime measurement techniques. As discussed in S. Bowden and R. A. Sinton 'Determining lifetime in silicon blocks and wafers with accurate expressions for carrier density', *Journal of Applied Physics* 102, 124501 (2007) for the QSSPC technique for example, lifetime data can be reported either for constant illumination intensity (i.e. constant G), resulting in a different injection level for each effective lifetime (as is the case e.g. in PL images on wafers), or for constant injection level, equivalent to reporting each lifetime for a different illumination intensity. Both approaches have shortcomings in that they report data within specific lifetime ranges either at an injection level or at an illumination intensity (or both) that may have little or no relevance to the operation of a solar cell.

In contrast, we have surprisingly found that a single PL image on a bulk silicon sample (such as a brick) allows measurement of the bulk lifetime at a constant illumination level and at a constant well-defined average injection level over a wide range of bulk lifetimes. To understand this counter-intuitive result we need to consider the definition of average carrier density and generation rate. In lifetime measurements on wafers, $\Delta n$ and G are commonly calculated as mean values averaged over the sample thickness. However as was pointed out in the abovementioned Bowden and Sinton paper, this approach is not meaningful for bulk samples such as bricks, because relative to the total sample thickness, significant excess carriers are present only in a small volume near the illuminated surface (compare for example the carrier density profiles shown in FIGS. 5(a) and 5(b)). Bowden and Sinton described an analytical methodology that overcomes this problem by defining a weighted average carrier density $\Delta n_{avg}$ and an effective sample width $W_{eff}$. We adopt those definitions here and use the notation of average excess carrier density accordingly.

Using the analytical model described in the abovementioned Bowden and Sinton paper, excess carrier density was calculated as a function of position inside an unpassivated silicon brick for two values of the absorption coefficient ($\alpha=700$ cm$^{-1}$, corresponding to ~800 nm incident light, and $\alpha=3.5$ cm$^{-1}$, corresponding to ~1100 nm incident light) and plotted in FIGS. 5(a) and 5(b) respectively. Note that the excess carrier density is zero at the surface (position=0) because the surface is unpassivated. FIGS. 5(a) and 5(b) both show excess carrier density versus position for three values of bulk lifetime: 10 µs (plot 18), 100 µs (plot 20), and 1000 µs (plot 22). In each graph the intersections of the rectangles 40 (shown only for the $\tau_{bulk}=100$ µs and $\tau_{bulk}=1000$ µs plots) with the axes indicate the values of $\Delta n_{avg}$ and $W_{eff}$. Comparison of the rectangles shown for short wavelength excitation ($\alpha=700$ cm$^{-1}$) in FIG. 5(a) shows that the main variation in the carrier profile with increasing bulk lifetime is in the effective width, while the average carrier density is almost constant. The same comparison for long wavelength excitation ($\alpha=3.5$ cm$^{-1}$) shows that the average carrier density (related to the average injection level) scales strongly with lifetime.

These observations are consistent with the following equation derived by Bowden and Sinton:

$$\Delta n_{avg} = \frac{\alpha N_s L^2}{2D(\alpha L+1)^2} \quad (1)$$

where L is the diffusion length, D the diffusion coefficient, $N_s$ the photon flux entering the sample, and $\alpha$ the absorption coefficient. For $\alpha L \gg 1$, i.e. for short wavelength excitation (or long lifetimes) eqn (1) simplifies to $$\Delta n_{avg} = \frac{N_s}{2D\alpha} \quad (2)$$

implying that the average injection level becomes independent of the lifetime. On the other hand for $\alpha L \ll 1$, i.e. for long wavelength excitation, and using the relation $\tau=L^2/D$, eqn (1) simplifies to $$\Delta n_{avg} = \frac{\alpha N_s \tau}{2} \quad (3)$$

implying that the average injection level is proportional to the lifetime $\tau$.

Turning now to consideration of the influence of injection level on PL data, we note that PL images are typically acquired with infrared excitation around $\lambda=800$ nm. With the absorption coefficient $\alpha \sim 700$ cm$^{-1}$ in this range, the condition $\alpha L \gg 1$ is fulfilled for $L \geq 100$ µm, a diffusion length equivalent to $\tau_{bulk}=3.5$ µs in p-type silicon. Importantly, in the most relevant range $\tau_{bulk}>3.5$ µs, a single PL image taken with laterally constant illumination and with $\lambda=800$ nm excitation thus yields variable lifetime at an almost constant average injection level. With D=27 cm$^2$s$^{-1}$ and $N_s=3*10^{17}$ cm$^{-2}$s$^{-1}$ (approximately equivalent to 1 Sun illumination), eqn (2) yields $\Delta n_{avg}=8*10^{12}$ cm$^{-3}$, independent of lifetime.

The choice of near infrared wavelengths around $\lambda=800$ nm for excitation thus has the added benefit that for typical bulk lifetimes it results in an average injection level in the brick that is very close to the injection level that would be present in a typical finished industrial silicon solar cell at the maximum power point. Variation of the excitation wavelength or of the illumination intensity (or both) allows fine tuning of that injection level as required. Measuring lifetime data in this injection level range also facilitates the analysis and avoids inaccuracies associated with injection level dependencies of material parameters such as the carrier mobilities or the radiative recombination coefficient, which vary significantly only at higher injection levels. Within the fundamental limitations of an analytical model that defines a spatially averaged injection level within a brick, PL imaging thus provides ideal conditions for bulk lifetime evaluation.

The small dependence of the average injection level on bulk lifetime in PL measurements taken with short wavelength excitation on bricks has another interesting implication, in that the injection level is then almost linearly dependent on the illumination intensity. Taking several luminescence images of the same brick area but with different illumination intensities allows measurement of the injection level dependent lifetime for each point or for specific areas in the image. This can be achieved by normalising the measured images with regard to the illumination intensity, followed by conversion of the intensity-normalised PL count into bulk lifetime, the latter conversion performed as described previously.

Since the average injection level is proportional to the generation rate G, which is itself proportional to the incident light intensity, a measured incident light intensity can be converted into an average injection level using eqn (1) or eqn (2). From a number of PL images taken with different illumination intensities, the injection level dependence of the bulk lifetime can thus be calculated and plotted for a specific area or a single pixel.

For comparison, we now consider the influence of injection level on QSSPC data. An example QSSPC tool, the Sinton Consulting 'boule tester', reports bulk lifetime as a function of injection level. Line scans of the estimated bulk lifetime are reported at a constant average carrier density, commonly at $\Delta n_{avg}=5*10^{14}$ cm$^{-3}$. Since a broad band light source is used in this system, a simple analytical solution is not possible. Assuming illumination with 1100 nm light ($\alpha=3.5$ cm$^{-1}$) the condition $\alpha L<1$ is fulfilled for bulk lifetimes $\tau_{bulk}<3$ ms, and in this range the average injection level scales with the bulk lifetime according to eqns (1) and (3), similar to the usual case of lifetime measurements on wafers. With 1 Sun equivalent illumination intensity ($N_s=3*10^{17}$ cm$^{-2}$s$^{-1}$) and $\alpha=3.5$ cm$^{-1}$ we calculate $\Delta n_{avg}=4.7*10^{12}$ cm$^{-3}$ and $\Delta n_{avg}=3.7*10^{13}$ cm$^{-3}$ for $\tau_{bulk}=10$ μs and $\tau_{bulk}=100$ μs respectively according to eqn (1). To achieve the commonly reported average carrier density of $\Delta n_{avg}=5*10^{14}$ cm$^{-3}$, an incident light intensity of about 100 Suns ($N_s=3*10^{19}$ cm$^{-2}$s$^{-1}$) is thus required for $\tau_{bulk}=10$ μs. Shorter lifetimes reported at $\Delta n_{avg}=5*10^{14}$ cm$^{-3}$ would require even larger light intensities. Note that these intensity factors depend strongly on the exact spectral content in the light intensity profile, but these figures show that large light intensities are generally required in typical QSSPC measurements to achieve $\Delta n_{avg}=5*10^{14}$ cm$^{-3}$. These light intensities are unrealistic for conventional solar cell applications since solar cells are normally operated at one Sun equivalent illumination and at an operating point that reduces the carrier density inside the wafer to a value that would be achieved at 0.05 Suns under open circuit conditions. Lifetime data reported for tens or hundreds of Suns therefore have only limited relevance for solar cell applications.

In the description provided herein, numerous specific details are set forth. However, it is understood that embodiments of the invention may be practised without these specific details. In other instances, well-known methods, structures and techniques have not been shown in detail in order not to obscure an understanding of this description.

Although the present invention has been described with particular reference to certain preferred embodiments thereof, variations and modifications of the present invention can be effected within the spirit and scope of the following claims.

The invention claimed is:

1. A method of conducting an analysis of a silicon ingot or brick, said method including the steps of:
   (a) exciting at least one side facet of said silicon ingot or brick to produce photoluminescence;
   (b) obtaining at least one image of the photoluminescence emitted from said at least one side facet; and
   (c) interpreting said at least one image to identify variations in effective and/or bulk minority carrier lifetime in said ingot or brick, wherein the step of interpreting said at least one image comprises normalising the photoluminescence intensity within said at least one image with regard to variations in the background doping density of said ingot or brick, to identify variations in effective minority carrier lifetime in said ingot or brick.

2. A method according to claim 1, wherein the normalised photoluminescence intensity is converted to bulk minority carrier lifetime data using a predetermined theoretical relationship.

3. A method according to claim 2, wherein the photoluminescence emitted from said at least one side facet is long-pass filtered to strengthen the dependence of the normalised photoluminescence intensity on bulk minority carrier lifetime.

4. A method according to claim 3, further comprising the step of correcting said at least one image for the angular dependence of the transmission of a filter used for the long-pass filtering.

5. A system when used to implement the method according to claim 1.

6. A method according to claim 2, wherein two or more images are obtained of photoluminescence produced with different illumination intensities, and said interpreting step comprises calculating the injection level dependence of the bulk minority carrier lifetime.

7. A method according to claim 1, wherein the normalised photoluminescence intensity is converted to bulk minority carrier lifetime data using a predetermined empirical relationship.

8. A method according to claim 7, wherein the photoluminescence emitted from said at least one side facet is long-pass filtered to strengthen the dependence of the normalised photoluminescence intensity on bulk minority carrier lifetime.

9. A method according to claim 8, further comprising the step of correcting said at least one image for the angular dependence of the transmission of a filter used for the long-pass filtering.

10. A method according to claim 7, wherein two or more images are obtained of photoluminescence produced with different illumination intensities, and said interpreting step comprises calculating the injection level dependence of the bulk minority carrier lifetime.

11. A method according to claim 1, wherein steps (a) and (b) are performed when scanning said ingot or brick and an illumination/detection system relative to each other.

12. A method of conducting an analysis of a silicon ingot or brick, said method including the steps of:
   (a) exciting at least one side facet of said silicon ingot or brick to produce photoluminescence;
   (b) obtaining at least one image of the photoluminescence emitted from said at least one side facet; and
   (c) interpreting said at least one image to identify variations in effective and/or bulk minority carrier lifetime in said ingot or brick,
   wherein the at least one photoluminescence image is used as a cutting guide in wafer production, or as a guide in wafer production to sort wafers into quality bins.

13. A method of conducting an analysis of a silicon ingot or brick, said method including the steps of:
   (a) exciting at least one side facet of said silicon ingot or brick to produce photoluminescence;
   (b) obtaining at least one image of the photoluminescence emitted from said at least one side facet; and
   (c) interpreting said at least one image to identify variations in effective and/or bulk minority carrier lifetime in said ingot or brick,
   wherein the information obtained from said method is used in the manufacturing of silicon bricks or ingots, or to determine the price of wafers derived from said ingot or brick, or to obtain feedback on feedstock quality in the production of silicon wafers.

14. A system for conducting an analysis of a silicon ingot or brick, said system comprising:
   a photodetection unit for obtaining at least one image or line scan of photoluminescence generated from at least one side facet of said silicon ingot or brick; and
   a processor for interpreting said at least one photoluminescence image or line scan to identify variations in effective and/or bulk minority carrier lifetime in said ingot or brick wherein said processor is adapted to normalise the photoluminescence intensity within said at least one photoluminescence image or line scan with regard to variations in the background doping density of said ingot or brick, to identify variations in effective minority carrier lifetime in said ingot or brick.

15. A system according to claim 14, further comprising a long-pass filter for filtering the photoluminescence generated from said at least one side facet of said silicon ingot or brick.

16. A system according to claim 15, wherein said processor is adapted to correct said at least one image for the angular dependence of the transmission of said long-pass filter.

17. A system according to claim 14, further comprising a mechanism for scanning said photodetection unit and said ingot or brick relative to each other.

18. A system according to claim 14, further comprising:
   an optical source emitting light with wavelength longer than the band-gap of silicon; and
   a detector for measuring the transmission of said light through said silicon ingot or brick.

19. A system according to claim 14, wherein said processor is adapted to convert the normalised photoluminescence intensity to bulk minority carrier lifetime data using a predetermined theoretical or empirical relationship.

20. A system according to claim 19, wherein said processor is adapted to calculate the injection level dependence of the bulk minority carrier lifetime using two or more images of photoluminescence produced with different illumination intensities.

21. A system for conducting an analysis of a silicon ingot or brick, said system including:
   a photodetection unit for obtaining at least one image or line scan of photoluminescence generated from at least one side facet of said silicon ingot or brick; and
   a processor for interpreting said at least one photoluminescence image or line scan to identify variations in effective and/or bulk minority carrier lifetime in said ingot or brick,
   wherein said processor is adapted to obtain information from said at least one photoluminescence image for use as a cutting guide in wafer production, or in the manufacturing of silicon bricks or ingots, or in determining the price of wafers derived from said ingot or brick, or as a guide in wafer production for sorting wafers into quality bins, or in obtaining feedback on feedstock quality in the production of silicon wafers.

\* \* \* \* \*